(12) United States Patent
Sakuta

(10) Patent No.: US 6,747,115 B2
(45) Date of Patent: Jun. 8, 2004

(54) SILICONE POLYMER, SILICONE COMPOSITION, AND COSMETIC PREPARATION CONTAINING THE SAME

(75) Inventor: Koji Sakuta, Gunma (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/296,593

(22) PCT Filed: May 22, 2001

(86) PCT No.: PCT/JP01/04249

§ 371 (c)(1), (2), (4) Date: Nov. 26, 2002

(87) PCT Pub. No.: WO01/92375

PCT Pub. Date: Dec. 6, 2001

(65) Prior Publication Data

US 2003/0199660 A1 Oct. 23, 2003

(30) Foreign Application Priority Data

May 31, 2000 (JP) ........................................ 2000-162940

(51) Int. Cl.$^7$ ................................................ C08G 77/24
(52) U.S. Cl. .............................. 528/31; 528/29; 528/31; 528/42; 424/401; 556/445
(58) Field of Search .............................. 528/28, 31, 32, 528/42, 29; 424/401; 556/445

(56) References Cited

U.S. PATENT DOCUMENTS

| | | | | |
|---|---|---|---|---|
| 5,043,464 A | * | 8/1991 | Yamamoto | ................... 556/437 |
| 5,112,512 A | * | 5/1992 | Nakamura | ................... 252/62.2 |
| 5,236,986 A | | 8/1993 | Sakuta | |
| 5,412,004 A | * | 5/1995 | Tachibana et al. | ............. 524/27 |
| 5,446,114 A | * | 8/1995 | O'Lenick, Jr. | ................ 528/15 |
| 5,698,655 A | * | 12/1997 | Chung et al. | ................... 528/29 |

FOREIGN PATENT DOCUMENTS

| | | |
|---|---|---|
| EP | 501791 A2 | 2/1992 |
| EP | 896015 A1 | 8/1998 |
| JP | 2000-26737 A | 1/2000 |

* cited by examiner

Primary Examiner—Margaret G. Moore
(74) Attorney, Agent, or Firm—Millen, White, Zelano & Branigan, P.C.

(57) ABSTRACT

This invention relates to a silicone polymer that is insoluble in organic solvents due to its three dimensional crosslinked structure which swells up relative to fluorosilicone oils. The silicone polymer is a crosslinked product of an SiH containing fluorosilicone and an unsaturated polyoxyalkylene. This invention also relates to a paste-like composition formed by making the silicone compounds swell up in silicone oil and a cosmetic material.

37 Claims, No Drawings

SILICONE POLYMER, SILICONE COMPOSITION, AND COSMETIC PREPARATION CONTAINING THE SAME

FIELD OF THE INVENTION

This invention relates to a silicone polymer which is insoluble in organic solvents because it has a three-dimensional crosslinked structure which swells up relative to fluorosilicone oils, to a paste-like composition formed by making the silicone compounds swell up in silicone oil, and to a cosmetic material.

BACKGROUND OF THE INVENTION

In various fields including that of cosmetic products, silicone oils have long been used as base oils on account of their safety.

In particular, with regard to skin care and make up, low viscosity silicone oils of 100 mm$^2$/s are very popular on account of their excellent spreading properties, clean feel and high safety.

However, when for example a paste composition without fluidity is made up with a low viscosity silicone oil as base oil, the addition amount of thickener has to be increased, and consequently it is difficult to obtain a smooth, even composition. Moreover, the low viscosity silicone oil tends to separate and leak from the composition obtained, so stability was low. To solve this problem, organic materials such as dextrin fatty acid esters (Japanese Patent Laid-Open Sho 62-121764, 62-143971, 62-143970, 63-159489), cane sugar fatty acid esters (Japanese Patent Laid-Open Sho 63-235366), trimethylsilyl polyvinyl alcohol or trimethyl silyl oligosaccharides (Japanese Patent Laid-Open Sho 62-240335) and fatty acid ester group-containing cellulose ethers (Japanese Patent Laid-Open Sho 63-260955), or inorganic materials such as organically modified clay minerals (Japanese Patent Laid-Open Sho 62-45656, 62-54759, 63-72779), have been used as thickeners for low viscosity silicone oils.

However, when these organic or inorganic materials were used as thickeners, there was a problem in that the clean feel and high extendibility of the low viscosity silicone oil decline.

In this connection, a method was proposed obtain a uniform paste-like composition by using a specific silicone polymer as a thickener, and treating the low viscosity silicone oil under a shear force (Japanese Patent Laid-Open 2-43263).

However, in the field of cosmetic products, not only oil but also water must be blended with the composition as an essential component. In this case, surfactants are used according to the normal procedure, but it is difficult to disperse the silicone oil and water in a homogeneous, stable state. Also, although the silicone thickener disclosed in the aforesaid Japanese Patent Laid-Open 2-43263 has excellent thickening properties relative to the silicone oil, it does not disperse evenly when water is also blended in the composition. Moreover, some surfactants irritate the skin, and their use is therefore undesirable.

To solve this disadvantage, in Japanese Patent Laid-Open Hei 4-272932, and 5-140320, it was proposed to introduce a polyoxyalkylene group in the molecule of the silicone thickener.

At the same time, to improve the staying powers of the cosmetic material, it has been proposed to blend a silicone oil having excellent water repellence and oil repellence and a high fluorine content with the silicone oil. However, although these oils have a high water repellence and oil repellence, water and oil tend to separate from them in storage. Consequently, it was difficult to obtain a cosmetic material having excellent storage stability, and excellent functional properties when it was used on the skin.

Problems Which This Invention Attempts to Solve

It is therefore an object of this invention to provide a silicone polymer having a fluorine-modified oil with excellent water repellence and oil repellence as base oil, and which swells up relative to these oils, to a homogeneous paste-like composition using this silicone polymer, and to a cosmetic material comprising this composition.

Means to Solve the Above Problems

This invention, which was discovered as a result of intensive studies performed to achieve the above object, is a silicone polymer having a three-dimensional crosslinked structure obtained by polymerizing at least one selected from the group consisting of an organohydrogen polysiloxane represented by the general formula (A1):

$$R^1{}_aR^2{}_bH_cSiO_{(4-a-b-c)/2}, \qquad (A1)$$

and an organohydrogen polysiloxane represented by the general formula (A2):

$$R^1{}_dH_eSiO_{(4-d-e)/2}, \qquad (A2)$$

and at least one selected from the group consisting of a polyoxyalkylene represented by the following general formula (B1):

$$C_jH_{2f-10}(C_gH_{2g}O)_nC_jH_{2f-1}, \qquad (B1)$$

a polyoxyalkylene represented by the following general formula (B2):

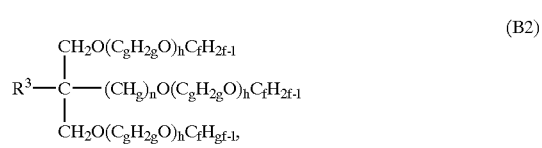

(B2)
$$\begin{array}{c} CH_2O(C_gH_{2g}O)_hC_fH_{2f-1} \\ | \\ R^3-C-(CH_g)_nO(C_gH_{2g}O)_hC_fH_{2f-1} \\ | \\ CH_2O(C_gH_{2g}O)_hC_fH_{gf-1}, \end{array}$$

a polyoxyalkylene represented the following general formula (B3):

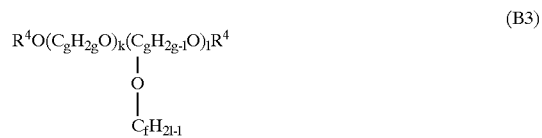

(B3)
$$\begin{array}{c} R^4O(C_gH_{2g}O)_k(C_gH_{2g-1}O)_lR^4 \\ | \\ O \\ | \\ C_fH_{2l-1} \end{array}$$

and an organopolyoxy alkylene (B4) represented by the following general formula (B4):

$$R^1{}_jR^5{}_kSiO_{(4-j-k)/2}, \qquad (B4)$$

which can contain (or dissolve and swell) its same weight or more of pentane-3,3,3-trifluoropropyl pentamethylcyclopentasiloxane (in the formula, $R^1$, which may be the same or different, is a hydrocarbon group having 1 to 20 carbon atoms, which do not contain an aliphatic unsaturated bond and may be substituted or unsubstituted, whereof about 11 to 60 mole % is a fluorine-substituted monovalent hydrocarbon group, $R^2$, which may be the same or different, is an organic group represented by the general formula $—C_fH_{2f}O(C_gH_{2g}O)_nR^6$, $R^3$, which may be the same or different, is hydrogen atom or a monofunctional hydrocarbon group containing 1 to 10 carbon atoms which does not contain aliphatic unsaturated bonds and which may be substituted or unsubstituted, $R^4$, which may be the same or different, is an organic group identical to $R^3$ or represented by $—C_jH_{2j-1}$, $R^5$ is a monofunctional hydrocarbon group having 2 to 10 carbon atoms containing a terminal vinyl group, and $R^6$ is a hydrogen atom or a monofunctional hydrocarbon group or acetyl group not containing aliphatic unsaturated groups, which may be substituted or and substituted, a is about 1.0–2.3, b is about 0.001 to 1.0, c is about 0.001–1.0, d is about 1.0–2.3, e is about 0.001–1.0, j is about 1.0–2.3, and k is about 0.001–1.0, and about $1.5 \leq a+b+c \leq$ about 2.6, about $1.5 \leq d+e \leq$ about 2.6, about $1.5 \leq j+k \leq$ about 2.6, f is an integer in the range 2–6, g is 2, 3 or 4, h is an integer in the range 1–200, i is an integer in the range 1–20, and x is 0 or 1. ).

The silicone polymer obtained by polymerizing the organohydrogen polysiloxane expressed by the above general formula (A2) and the organopolysiloxane expressed by the above general formula (B4), or the silicone polymer obtained by polymerizing the organohydrogen polysiloxane expressed by the above general formula (A2) and the polyoxyalkylene expressed by the above general formula (B1), are preferred.

The paste-like silicone composition obtained by kneading a mixture of 100 weight parts of the above silicone polymer and 10–1000 weight parts of a fluorine-modified silicone oil, which is represented by the general formula (C):

$$R^1_m SiO_{(4-m)/2} \quad (C)$$

having a viscosity of less than about 200 mm$^2$/s at 25 degree C. ($R^1$ may be identical or different, are monofunctional hydrocarbon groups having 1 to 20 carbon atoms not containing an aliphatic unsaturated bond which may be substituted or unsubstituted, whereof about 11–60 mole % is a fluorine-substituted monofunctional hydrocarbon group, and m is 1.8–2.3), is a homogeneous paste, and cosmetic materials containing this paste-like silicone composition have good stability and are very easy-to-use.

This invention provides a cosmetic material wherein the above paste-like silicone composition is blended, or a cosmetic material comprising this cosmetic material as a component, comprising a) the above paste-like silicone composition, b) an oil and c) a compound having an alcoholic hydroxyl group in the molecular structure, wherein the blending amount of the a) paste-like silicone composition in the cosmetic material is 0.1–70.0 wt %.

At least part of this b) oil may be a liquid at ordinary temperature, and it is preferred that at least part of the oil b) is selected from the group consisting of a silicone oil comprising a volatile silicone, and an oil having a repeating unit of $—[O—Si—]n$ in the molecular skeleton. Herein, the "oil having a repeating unit of $—[O—Si—]n$ in the molecular skeleton" is an oil having a branched siloxane structure, which is a straight chain or cyclic silicone, whereof the major part comprises a $—[O—Si—]n$ skeleton and has a $—Si—(CH_2CH_2)_m—Si—$ bond in part of the molecule.

The compound c) having an alcoholic hydroxyl group in the molecular structure is preferably a water-soluble, and monofunctional or polyfunctional alcohol. The blending amount of the above oil b) is preferably 0.1 to 50.0 wt %, and the blending amount of the compound c) having an alcoholic hydroxyl group in the molecular structure is preferably 0.1 to 70.0 wt %.

The cosmetic material may also contain at least one of d) water, e) a powder and/or colorant, f) a surfactant, g) a crosslinked organopolysiloxane not containing a fluorine-substituted alkyl group, h) a silicone resin, and i) an ultraviolet protection component.

At least part of the above e) powder and/or colorant is preferably at least one of a powder having a silicon resin and silicone elastomer as skeleton, and an organic powder having $—[O—Si—]_n—$ as structural repeating unit in the molecular skeleton.

The f) surfactant is preferably a modified silicone having a polyoxy alkylene chain in the molecule, examples of this modified silicone being preferably represented by the following general formula (D):

(in the formula, $R^2$ are identical or different, and are organic groups represented by the general formula $—C_fH_{2f}O(C_gH_{2g}O)_nR^6$, $R^3$ is a hydrogen atom or a monofunctional hydrocarbon group having 1 to 10 carbon atoms not containing aliphatic unsaturated bonds, and which may be substituted or unsubstituted, $R^6$ is a hydrogen atom or a monofunctional hydrocarbon group or acetone group not containing or aliphatic unsaturated groups and which may be substituted or unsubstituted, $R^7$ is a fluorine-substituted monofunctional hydrocarbon group not containing aliphatic unsaturated bonds, p is about 1.0–2.0, q is about 0.001–1.0, r is about 0.001–1.0, and about $1.5:5 \leq p+q+r \leq$ about 2.6). It is preferred that HLB of the g) surfactant is 1–18.

The g) crosslinked organopolysiloxane not containing fluorine-substituted alkyl groups preferably contains (or dissolves) at least its own weight of a silicone having a viscosity of 0.65–100 mm$^2$/s, and swells up. It is more preferred that it is a crosslinked organopolysiloxane which forms a crosslinked structure by reacting an organopolysiloxane having at least an average of 1.5 vinylic reactive sites, and an organopolysiloxane having at least an average of 1.5 hydrogen atoms directly bonded to silicon atoms, in the molecule. In particular, it is further preferred that this g) crosslinked organopolysiloxane not containing fluorine-substituted alkyl groups is a crosslinked organopolysiloxane comprising at least one of a polyoxyalkyl part, alkyl part, alkenyl part and aryl part in the crosslinked molecule.

It is preferred that the h) silicone resin is an acrylic silicone, and more preferred that this acrylic silicone contains at least one of a pyrrolidone part, long chain alkyl part, polyoxyalkylene part and fluoroalkyl part in the molecule. Further, it is preferred that the h) silicone resin is a silicone lattice compound, and more preferred that this silicone lattice compound contains at least one of a pyrrolidone part, long chain alkyl part, polyoxyalkylene part, fluoroalkyl part and amino part.

This invention provides a skincare cosmetic, hair treatment cosmetic, antiperspirant, make-up or ultraviolet protection cosmetic, and further provides a cosmetic of this type in the form of a liquid, and emulsion, cream, solid, paste, gel, powder, laminate, mousse or spray.

Description of the Embodiments

Describing the invention now in more detail, the component (A1) is represented by the average empirical formula $R^1_a R^2_b H_c SiO_{(4-a-b-b)/2}$ (($R^1$ may be identical or different, and are monofunctional hydrocarbon groups having 1 to 20 carbon atoms not containing an aliphatic unsaturated bond which may be substituted or unsubstituted, whereof 11–60 mole % is a fluorine-substituted monofunctional hydrocarbon group), $R^2$ may be identical or different, and are organic groups represented by the general formula —$C_fH_{2f}O(C_gH_{2g}O)_hR^6$, a, b, c are integers satisfying the relations $1.0 \leq a \leq 2.3$, $0.001 \leq b \leq 1.0$, $0.001 \leq c \leq 1.0$, $1.5 \leq a+b+c \leq 2.6$, f is an integer in the range 2–6, g is 2 and/or 3, and/or 4, h is an integer in the range 1–200, and $R^6$ is a monofunctional hydrocarbon group or acetyl group not containing hydrogen atoms or aliphatic unsaturated groups, which may be substituted or unsubstituted).

Examples of $R^1$ are alkyl groups such as methyl, ethyl, propyl, butyl, pentyl, hexyl, heptyl, octyl, nonyl and decyl; saturated alicyclic hydrocarbons such as cyclopentyl and cyclohexyl; aryl groups such as phenyl and tolyl; and fluorine-substituted alkyl groups such as trifluoropropyl, nonafluorohexyl and heptadecylfluorodecyl, but methyl and trifluoropropyl are particularly to be preferred.

Of the organic groups $R^1$, it is required that 11–60 mol % are fluorine-substituted monofunctional hydrocarbon groups. If the proportion is less than 11 mole %, swelling properties in the fluorine-substituted silicone oil which is component (C) become poorer, and if it exceeds 60 mol %, manufacture of the component (A1) is difficult. Preferably, the range is 20–50 mole %.

a is 1.0–2.3, but preferably 1.2–2.1. b is 0.001–1.0, but preferably 0.005–0.5. c is 0.001–1.0, but preferably 0.005–0.5. When a is less than 1.0, the degree of crosslinking is too high, so the polymer cannot contain its own weight or more of penta-3,3,3-trifluoropropyl pentamethyl cyclopentasiloxane, and when it is larger than 2.3, the degree of crosslinking is too low, so it is difficult to form the three-dimensional crosslinked structure. When b is less than 0.001, the hydrophilic properties are low, so it is difficult to form a water-in-oil (W/O) composition, and when it is larger than 1.0, hydrophilic properties are too high so it is again difficult to form a water-in-oil emulsion composition. When c is less than 0.001, the degree of crosslinking is low, so it is difficult to form a three-dimensional crosslinked structure, and when it is larger than 1.0, the degree of crosslinking is too high, so the polymer can no longer contain its own weight or more of penta-3,3,3-trifluoropropyl pentamethyl cyclopentasiloxane.

a+b+c is in the range 1.51–2.6, but preferably 1.8–2.2. f is in the range 2–6, but preferably 3–6. g is 2 and/or 3, and/or 4. At least one unit is selected from ethylene oxide, propylene oxide and butylene oxide, but ethylene oxide or a copolymer of ethylene oxide and propylene oxide is preferred. h is an integer in the range 1–200, but preferably 3–100. Examples of $R^6$ are hydrogen, methyl, heptyl, propyl, butyl, pentyl, hexyl, heptyl, octyl, nonyl, decyl and acetyl, but hydrogen or methyl are particularly preferred.

This organopolysiloxane may be straight chain, branched or cyclic, but to make the polymerization reaction proceed smoothly, it is preferred that it is straight chain or essentially straight chain, and partly contains branch units.

The component (A2) is represented by the average empirical formula $R^1_dH_eSiO_{(4-d-e-)/2}$ (in the formula, $R^1$ may be the same as above, and d, e are integers satisfying the relation $1.0 \leq d \leq 2.3$, $0.001 \leq e \leq 1.0$).

d is 1.0–2.3, but preferably 1.2–2.1, and e is 0.001–1.0, but preferably 0.005–0.5. When d is less than 1.0, the degree of crosslinking is too high, so the polymer cannot contain its own weight or more of penta-3,3, 3-trifluoropropyl pentamethylcyclopentasiloxane. When it is larger than 2.3, the degree of crosslinking is too low, so it is difficult to form the three-dimensional crosslinked structure. When e is less than 0.001, the degree of crosslinking is too low, so it is difficult to form the three-dimensional crosslinked structure, and when it is larger than 1.0, the degree of crosslinking is too high, so the polymer can no longer contain its own weight or more of penta-3,3,3-trifluoropropyl pentamethylcyclopentasiloxane.

This organopolysiloxane may be straight chain, branched or cyclic, but to make the polymerization reaction proceed smoothly, it is preferred that it is straight chain or essentially straight chain, and partly contains branch units.

The component (B1) is represented by the average empirical formula $C_fH_{2f-1}(C_gH_{2g}O)C_fH_{2f-1}$ (in the formula, f, g and h are identical to the above).

The component (B2) has the average empirical formula:

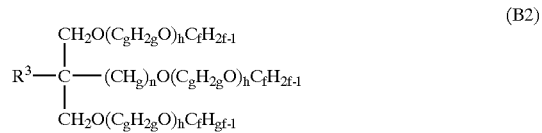

(B2)

(in the formula, $R^3$ is a monofunctional hydrocarbon group of 1–10 carbon atoms not containing hydrogen atoms or aliphatic unsaturated group bonds, and which may be substituted or unsubstituted, f, g and h are identical to the above, and x is 0 or 1).

Examples of $R^3$ are hydrogen, methyl, ethyl, propyl, butyl, pentyl, hexyl, heptyl, octyl, nonyl and decyl, but hydrogen, methyl, ethyl and propyl are particularly preferred.

The component. (B2) may be obtained for example using glycerine or trimethyloylpropane as starting material by alkenyl etheration of the terminal groups.

All three polyoxyalkylene terminal groups are alkenyl etherated, but only two may be blocked by alkenyl ether, and and the remaining one left as a hydroxyl group.

If the component (B2) is obtained using glycerine monoallyl ether or trimethyloylpropane monoallyl ether as starting material by adding an alkenyl oxide and performing alkenyl etheration of the terminal groups, a structure is obtained containing two polyoxyalkylene units in the molecule and three terminal alkenyl groups in the molecule. This polyoxyalkylene compound may also be used.

The component (B3) may be represented by the average empirical formula:

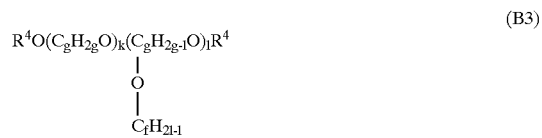

(B3)

(in the formula, $R^4$ are organic groups which may be identical or different, and are identical to $R^3$ or represented by —$C_fH_{2f-1}$, f, g and h are identical to the above, and i is integer in the range 1–20).

i is 1–20, but preferably 2–10. When i is larger than 20, the degree of crosslinking is too high, so the polymer can no longer contain its own weight or more of penta-3,3,3-trifluoropropyl pentamethylcyclopentasiloxane.

The component (B3) may for example be obtained by adding an alkylene oxide and allyl glycidyl ether to a lower alcohol or allyl alcohol, or by alkylation or alkenyl etheration of terminal groups after the addition.

The component (B4) has the average empirical formula $R^1_jR^5_kSiO_{(4-j-k)/2}$ (in the formula, $R^1$ is identical to the above, $R^5$ is a monofunctional hydrocarbon group having terminal vinyl groups, and j, k are integers satisfying the relations $1.0 \leq j \leq 2.3$, $0.001 \leq k \leq 1.0$). Examples of $R^5$ are vinyl, allyl, butenyl, pentenyl, hexenyl, heptenyl, octenyl, nonenyl and decenyl, but vinyl is preferred. j is 1.0–2.3, but preferably 1.2–2.1, k is 0.001–1.0, but preferably 0.005–0.5. When j is less than 1.0, the degree of crosslinking is too high, so the polymer can no longer contain its own weight or more of penta-3,3,3-trifluoropropyl pentamethyl cyclopentasiloxane. When it is larger than 2.3, the degree of crosslinking is too low, so it is difficult to form a three-dimensional crosslinked structure. When k is less than 0.001, the degree of crosslinking is too low, so it is difficult to form a three-dimensional crosslinked structure, and when it is larger than 1.0, the degree of crosslinking is too high, so the polymer can no longer contain its own weight or more of penta-3,3,3-trifluoropropyl pentamethyl cyclopentasiloxane.

This organopolysiloxane may be straight chain, branched or cyclic, but to make the polymerization reaction proceed smoothly, it is preferred that it is straight chain or essentially straight chain, and partly contains branch units.

The component (C) is represented by the average empirical formula $R^1_m SiO_{(4-m)/2}$ (in the formula, $R^1$ is identical to the above and m is an integer satisfying the relation $1.8 \leq m \leq 52.3$). m lies in the range 1.8–2.3, but preferably 1.9–2.1. This organopolysiloxane may be straight chain, branched or cyclic, but it is preferred that it is straight chain or essentially straight chain, and partly comprises a branch unit. It is particularly preferred that it is a fluorine-modified cyclic silicone represented by the formula:

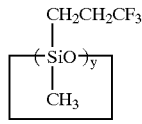

(in the formula, y is an integer from 4–6).

This fluorine-modified silicone oil has a viscosity at 25 degree C. of 200 mm²/s, but preferably 20–180 mm²/s.

The silicone polymer of this invention may be obtained by polymerizing the organohydrogen polysiloxanes represented by (A1) and/or (A2); the polyoxy alkylenes represented by (B1) and/or (B2), and/or (B3), and/or the organopolysiloxane represented by (B4). By kneading this silicone polymer with the fluoride-modified silicone oil (C), a paste-like composition can be obtained. Alternatively, a paste-like composition can be obtained by manufacturing a silicone polymer by polymerizing a mixture comprising the organohydrogen polysiloxanes represented by (A1) and/or (A2), the polyoxy alkylenes represented by (B1) and/or (B2), and/or (B3), and/or the organopolysiloxane represented by (Be), and part of the fluorine-modified silicone oil (C), and kneading this silicone polymer with the remainder of the fluoride-modified silicone oil (C).

To obtain the silicone polymer of this invention, the reaction is performed at room temperature or higher temperature (approx. 50–120 degree C.) in the presence of a platinum compound (e.g., platinic chloride, alcohol-modified platinic chloride or platinic acid chloride-vinyl siloxane complex), or a rhodium compound.

When the reaction is performed, it may be in the absence of a solvent or an organic solvent may be used if necessary. Examples of organic solvents are aliphatic alcohols such as methanol, ethanol, 2-propanol and butanol; aromatic hydrocarbons such as benzene, toluene and xylene; aliphatic or alicyclic hydrocarbons such as n-pentane, n-hexane and cyclohexane; halogenated hydrocarbons such as dichloromethane, chloroform and carbon tetrachloride; and ketone-type solvents such as acetone and methyl ketone. However, due to the intended use in cosmetic products, it is preferred to conduct the reaction in the absence of a solvent, or in ethanol or 2-propanol.

The silicone compound of this invention comprises a three-dimensional crosslinked structure which is insoluble in organic solvents, i.e., it is insoluble in organic solvents comprising aliphatic organic solvents such as straight chain or branched pentanes, hexane, decane, dodecane, hexadecane and octadecane; aromatic organic solvents such as benzene, toluene and xylene; alcohol-type organic solvents such as methanol, ethanol, propanol, butanol, hexanol and decanol; halogenated organic solvents such as chloroform and carbon tetrachloride; ketone-type organic solvents such as acetone and methylethyl ketone, and silicone solvents such as low viscosity dimethyl polysiloxane, methylphenyl polysiloxane and cyclic dimethyl polysiloxane.

The silicone polymer of this invention can also contain at least its own weight pentane-3,3,3-trifluoropropyl pentamethylcyclopentasiloxane, and a method of confirming this will be described later.

In the manufacture of the silicone composition of this invention, when the silicone polymer (C) is kneaded with the fluorine-modified silicone oil, this may be accomplished by an ordinary stirrer, but it is preferably performed under a shear force. This is because the silicone polymer has a three-dimensional crosslinked structure insoluble in solvents and the silicone polymer and the component (C) do not blend together homogeneously, so a paste-like composition of smooth appearance must be obtained by supplying sufficient dispersion.

The kneading may be performed for example by a three roller roll mill, two roller mill, side grinder, colloid mill, Gowling homogeniser or Disper, but a three roller roll mill or a D spur are preferred.

The proportion of the silicone composition a) in the cosmetic material of this invention is in the range 0.1–70.0 wt %, but preferably 1.0 to 50.0 wt %. If it is less than 0.1%, the cosmetic material obtained using it does not have good storage stability, and if it exceeds 70.0%, it no longer has a clean feel when spread on the skin.

The oil b) which is a component of this invention may be any of the following. Examples of natural animal or vegetable oils and fats, and semi-synthetic oils and fats, are avocado oil, linseed oil, almond oil, Chinese wax, perilla oil, olive oil, cacao butter, kapok wax, kaya oil, carnauba wax, liver oil, candellila wax, beef tallow, beef foot oil, beef bone fat, hydrogenated beef tallow, apricot kernel oil, spermaceti, hydrogenated oil, wheat germ oil, sesame oil, rice germ oil, rice-bran oil, sugar cane wax, sasanqua oil, safflower oil, shea butter, Chinese tung oil, cinnamon oil, jojoba wax, shellac wax, turtle oil, soybean oil, tea seed oil, tsubaki oil, evening primrose oil, corn oil, lard, rape seed oil, Japanese tung oil, rice-bran wax, germ oil, horse fat, persic oil, palm oil, palm kernel oil, castor oil, hydrogenated castor oil, caster oil fatty acid methyl ester, sunflower oil, grape seed oil, bayberry wax, jojoba oil, macadamia nut oil, bees wax, mink oil, cottonseed oil, cotton wax, Japan wax, haze kernel oil, montan wax, coconut oil, hydrogenated coconut oil, tricoconut oil fatty acid glyceride, mutton-tallow, peanut oil, lanolin, liquid lanolin, reduced lanolin, lanolin alcohol, hard lanolin, lanolin acetate, lanolin fatty acid isopropyl, hexyl laurate, POE lanolin alcohol ether, POE lanolin alcohol acetate, lanolin fatty acid polyethylene glycol, POE hydrogenated lanolin alcohol ether, and egg yolk oil.

Examples of hydrocarbon oils include ozokerite, squalane, squalene, ceresine, paraffin, paraffin wax, liquid paraffin, pristane, polyisobutylene, microcrystalline wax and Vaseline.

Examples of higher fatty acids include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid and 12-hydroxystearic acid.

Examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, POE cholesterol ether, monostearyl glycerin ether (batyl alcohol) and monooleyl glyceryl ether (cerakyl alcohol).

Examples of ester oils include diisobutyl adipate, 2-hexyldecyl adipate, di-2-heptylundecyl adipate, N-alkylglycol monoisostearates, isocetyl isostearate, trimethylolpropane triisostearic acid ester, ethylene glycol di-2-ethylhexanoic acid ester, cetyl 2-ethylhexanoate, trimethylolpropane tri-2-ethylhexanoic acid ester, pentaerythritol tetra-2-ethylhexanoic acid ester, cetyl octanoate, octyldodecyl gum ester, oleyl oleate, octyldodecyl oleate, decyl oleate, neopentyl glycol dicapric acid ester, triethyl citrate, 2-ethylhexyl cinnamate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethylocanoate, ethyl laurate, hexyl laurate, N-lauroyl-L-glutaminic acid 2-octyldodecyl ester, diisostearyl malic acid, dextrin palmitic acid ester, dextrin stearic acid ester, dextrin 2-ethylhexanic acid palmitic acid ester, cane sugar palmitic acid ester, cane sugar stearic acid ester, monobenzylidene sorbitol and dibenzylidene sorbitol.

Examples of glyceride oils include acetoglyceride, diisooctanoic acid glyceride, triisostearic acid glyceride, triisopalmitic acidglyceride, tri-2-ethylhexanoic acid glyceride, monostearic acid glyceride, di-2-heptylundecanoic acid glyceride and trimyristic acid glyceride.

As examples of silicone oils, mention may be made of organopolysiloxanes of low to high viscosity such as dimethylpolysiloxane, methylphenyl-polysiloxane, methylhydrogenpolysiloxane and dimethylsiloxane-methylphenylsiloxane copolymer, cyclic siloxanes such as octamethylcyclotetrasiloxane, decamethylcyclopentasiloxane, dodecamethylcyclohexasiloxane, tetramethyltetrahydrogencyclotetra-siloxane and tetramethyltetraphenylcyclotetrasiloxane; silicone gums such as high polymer gum dimethylpolysiloxane and gum dimethylsiloxane-methylphenyl siloxane copolymer; and cyclic siloxane solutions of silicone gums, trimethylsiloxysilicic acid and cyclic siloxane solutions of trimethylsiloxysilicic acid, higher alkoxy-modified silicones such as stearoxysilicone, higher fatty acid-modified silicones, alkyl-modified silicones, amino-modified silicones, fluorine-modified silicones, silicone resins and silicone rubbers.

As examples of fluorine-containing oils, mention may be made of perfluoropolyether, perfluorodecalin, perfluorooctane, fluorinated pitch and fluoroalcohols. One, two or more of these may be used as necessary.

The content of the oil b) in the cosmetic material this invention depends on the form of the cosmetic material, but lies in the range 0–50.0 wt %, and preferably 1.0–30 wt %. If this content is less than 0.1 wt %, the slippery feel and moisture-retaining effect of the oil b) cannot be obtained, and if it exceeds 50.0 wt %, storage stability declines.

Examples of the compound c) having an alcoholic hydroxyl group in the molecular structure, which is a component of this invention, are as follows.

Examples of alcohols are lower alcohols such as ethanol, propanol and isopropanol; polyfunctional alcohols such as ethylene glycol, propylene glycol 1,3-butylene glycol, glycerine and diglycerine; alcohols such as ethylene glycol monoalkyl ether and diethylene glycol monoethylether; sugar alcohols such as sorbitol and mannitol; and cholesterol, sitostearol, phytosterol and lanosterol.

The water-soluble polymer may be a vegetable polymer such as gum arabic, gum tragacanth, galactan, carob gum, guar gum, karaya gum, carrageenan, pectin, agar, quince seed (marmelo), starch (rice, corn, potato, wheat), algae colloid, tranto gum and locust bean gum, microorganism polymers such as xanthan gum, dextran, saccinoglucan and pullulan, animal polymers such as collagen, casein, albumin and gelatin, starch polymers such as carboxymethyl starch and methylhydroxypropyl starch, cellulose polymers such as methyl cellulose, ethyl cellulose, methylhydroxypropyl cellulose, carboxymethyl cellulose, hydroxymethyl cellulose, hydroxypropyl cellulose, cellulose nitrate, cellulose sodium sulfate, sodium carboxymethyl cellulose, crystalline cellulose, and cellulose powder, alginic acid polymers such as sodium alginate and alginic acid propyleneglycol ester, vinyl polymers such as polyvinylmethylether and carboxyvinyl polymer, polyoxyethylene polymers, polyoxyethylene polyoxypropylene copolymer polymers, acrylic polymers such as sodium polyacrylate, polyethyl acrylate and polyacrylamide, other synthetic water-soluble polymers such as polyethyleneimine and cation polymers, and inorganic water-soluble polymers such as bentonite, magnesium aluminium silicate, laponite, hectorite and silicic acid anhydride.

Moreover, film-forming agents such as polyvinyl alcohol and polyvinyl pyrrolidone are also included in these water-soluble polymers, one, two or more being used as necessary. The content of the alcoholic hydroxyl group-containing compound c) in the cosmetic material this invention depends on the form of the cosmetic material, but lies in the range 0.1–70.0 wt %, and preferably 1.0–50 wt %. If this content is less than 0.1 wt %, the moisture-retaining, antifungal and antibiotic effects of c) cannot be obtained, and if it exceeds 50.0 wt %, the cosmetic material becomes stickier which is undesirable for cosmetic material.

Water d) may also be added as a component to the cosmetic material of this invention if required. The content of the water d) in the cosmetic material of this invention is 0–90.0 weight %, the blending proportion varying according to the type of cosmetic material. A cosmetic material containing water d) may take the form of an aqueous solution, oil-in-water (O/W) emulsion, water-in-oil.(W/0) emulsion, or an O/W/O or W/O/W emulsion.

An excellent cosmetic material according to the invention may be obtained using only the components b)-e), but the following components f), g), h), i), j) may also be added as required.

The component f) is the powders and/or colorants mentioned below. If used for ordinary cosmetic materials, the powder can take any form (spheres, needles, plates, non-defined forms, scales, spindles), have any particle diameter (haze, powders, pigments) and any particle structure (porous, non-porous). Examples are inorganic powders, organic powders, surfactant metal salt powders, colored pigments, pearl pigments, metal powder pigment and natural colorants.

Examples of inorganic powders are titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, red mica, biotite, lithia mica, silicic acid, silicic acid anhydride, aluminium silicate, magnesium silicate, magnesium aluminium silicate, calcium silicate, barium silicate, strontium silicate, tungstic acid metal salts, hydroxyapatite, vermiculite, haidingerite, bentonite, montmorillonite, hectorite, zeolite, ceramic powder, calcium diphosphate, alumina, aluminium hydroxide, boron nitride and silica.

Examples of organic powders are polyamide powder, polyester powder, polyethylene powder, polypropylene powder, polystyrene powder, polyurethane, benzoguanamine powder, polymethyl-benzoguanamine powder, tetrafluoroethylene powder, polymethylmethacrylate powder, cellulose, silk powder, nylon powder, nylon 12, nylon 6, silicone powder, styrene-acrylic acid copolymer, divinylbenzene-styrene copolymer, vinyl resin, urea resin, phenol resin, fluororesin, silicone resin, acrylic resin, melamine resin, epoxy resin, polycarbonate resin, microcrystalline fiber powders, starch powder and lauroyl lysine.

Examples of surfactant metal salt powders (metallic soaps) are zinc stearate, aluminum stearate, calcium stearate, magnesium stearate, zinc myristate, magnesium myristate, zinc cetyl phosphorate, calcium cetyl phosphate and zinc sodium cetyl phosphate.

Examples of colored pigments are inorganic red pigments such as ferric oxide, iron hydroxide and ferric titanate, inorganic brown pigments such as gamma-iron oxide, inorganic yellow pigments such as yellow iron oxide and ochre, inorganic black pigments such as black iron oxide and carbon black, inorganic purple pigments such as manganese violet and cobalt violet, inorganic green pigments such as chromium hydroxide, chromium oxide, cobalt oxide and cobalt titanate, inorganic blue pigments such as cobalt and titanic acid cobalt, Prussian blue and ultramarine blue, tar colorant lake, natural colorant lake, and synthetic resin powders comprising combinations of these powders.

Examples of pearl pigments are titanium oxide-coated mica, titanium oxide-coated mica, bismuth oxychloride, titanium oxide-coated bismuth oxychloride, titanium oxide-coated talc, scales foil and titanium oxide-coated colored mica; examples of metal powder pigments are aluminium powder, copper powder and stainless steel powder.

Examples of tar colorants are Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206 and Orange No. 207; examples of natural colorants are powders chosen from carminic acid, laccaic acid, carthamine, brazilin and crocin.

To the extent that it does not interfere with the purpose of this invention, complexes of these powders, or materials processed with common oil bases, silicone oils, fluorine compounds and surfactants may also be used if necessary.

Various types of surface pretreatment may or may not be performed such as for example fluorine compound treatment, silicone resin treatment, pendant treatment, silane coupling agent treatment, titanium coupling agent treatment, oil base treatment, N-acylation lysine treatment, polyacrylic acid treatment, metallic soap treatment, aminoacid treatment, anhydride treatment, plasma treatment or mechano-chemical treatment. One, two or more of the above may be used as required.

The blending proportion of the powder used depends on the form of the cosmetic material, but it is 0.1 to 50 wt %, and preferably 0.5 to 30 wt %, relative to the total weight of cosmetic material.

Of these powders, elastomers such as silicone elastomer spherical powder, polyethylene powder, polypropylene powder, poly tetrafluoroethylene powder, silicone gum powder and polyurethane powder are preferred, as the product is then stable over time and its feel improves.

The component f) is the surfactants shown below.

The surfactant may be anionic, cationic, non-ionic or amphoteric, there being no limitation thereupon provided it is used in ordinary cosmetic materials.

Specific examples of anionic surfactants are fatty acid soaps such as sodium stearate and triethanolamine palmitate, alkyl ether carboxylic acids and their salts, condensate salts of aminoacids and fatty acids, alkane sulfonates, alkene sulfonates, sulfonates of fatty acid esters, sulfonates of fatty acid amides, formalin condensation sulfonates, sulfate ester salts such as alkylsulfate ester salts, secondary higher alcohol sulfate ester salts, alkyl and allyl ether sulfate ester salts, sulfate ester salts of fatty acid esters, sulfate ester salts of fatty acid alkyloylamides and Turkey red oil, alkylphosphates, ether phosphates, alkyl allyl ether phosphates, amide phosphates and N-acyl aminoacid activators.

Specific examples of cationic surfactants are amino salts such as alkylamine salts, polyamines and aminoalcohol fatty acid derivatives, alkyl quartenary ammonium salts, aromatic quartenary ammonium salts, pyridium salts and imidazolium salts.

Examples of non-ionic surfactants are sorbitan fatty acid esters, glycerol fatty acid esters, polyglycerol fatty acid esters, propylene glycol fatty acid esters, polyethylene glycol fatty acid esters, cane sugar fatty acid esters, polyoxyethylene alkyl ethers, polyoxypropylene alkyl ethers, polyoxyethylene alkylphenyl ethers, polyoxyethylene fatty acid esters, polyoxyethylene sorbitan fatty acid esters, polyoxyethylene sorbitol fatty acid esters, polyoxyethylene glycerol fatty acid esters, polyoxyethylene propylene glycol fatty acid esters, polyoxyethylene castor oil, polyoxyethylene hardened castor oil, polyoxyethylene phytostanol ether, polyoxyethylene phytosterol ether, polyoxyethylene cholestanol ether, polyoxyethylene cholesterol ether, polyoxyalkylene-modified organopolysiloxanes, polyoxyalkylenealkyl co-modified organopolysiloxanes, alkanolamides, sugar ether and sugar amides.

Of non-ionic surfactants, the fluoroalkyl group-containing polyether-modified silicone represented by the average empirical formula $R^3_p R^2_q R^7_r SiO_{(4-p-q-r)/2}$ is preferred ($R^3$ and $R^2$ are the same as that of the above among a formula. $R^7$ is a fluorine-substituted monofunctional hydrocarbon having 1–10 carbon atoms which do not have an aliphatic unsaturated bond, and p, q, r are integers satisfying the relations $1.0 \leq p \leq 2.0$, $0.001 \leq q \leq 1.0$, $0.00 \leq r \leq 1.0$, and $1.5 \leq p+q+r \leq 2.6$, respectively).

Examples of $R^7$ are fluorine-substituted alkyl groups such as trifluoropropyl, nonafluorohexyl and heptadecylfluorodecyl, but trifluoropropyl is to be preferred.

p is 1.0–2.0, but preferably 1.2–1,9, q is 0.001–1.0, but preferably 0.005–0.5, and r is 0.001–1.0, but preferably 0.005–0.5. When p is less than 1.0, manufacture of this component is difficult, whereas if p exceeds 2.0, the fluorine-substituted alkyl group content is too low or hydrophilic properties are too low, so sufficient emulsification is no longer obtained. When q is less than 0.001, hydrophilic properties are too low, so sufficient emulsification is no longer obtained, and if it exceeds 1.0, manufacture of this component is difficult or, as the fluorine-substituted alkyl group content is too low, sufficient emulsification is again no longer obtained. When r is less than 0.001, hydrophilic properties are too low, the fluorine-substituted alkyl group content is too low, so sufficient emulsification is no longer obtained, and if it exceeds 1.0, manufacture of this component is difficult.

Examples of amphoteric surfactants are betaine, amino carboxylates and imidazoline derivatives. The blending amount relative to the surfactant is preferably 0.1–20 wt % and more preferably 0.5–10 wt % relative to the total amount of cosmetic material.

The component g) is a crosslinked organopolysiloxane which does not have a fluorine-substituted alkyl group, and it is preferred that this crosslinked organopolysiloxane contains more than its own weight of low viscosity silicone relative to silicone having a low viscosity of 0.65–100 mm$^2$/s. It is also preferred that the crosslinked organopolysiloxane is formed by reacting an organopolysiloxane having on average at least 1.5 vinylic reactive sites in the molecule, and an organohydrogen polysiloxane having at least 1.5 hydrogen atoms directly bonded to silicon atoms. Further, it is preferred that the crosslinked organopolysiloxane which does not contain this fluorine-substituted alkyl group, contains at least one species chosen from a group comprising a polyoxyalkylene part, an alkyl part, an alkenyl part, an aryl part or a fluoroalkyl part in the crosslinked molecule.

The blending amount of the crosslinked organopolysiloxane in use is preferably 0.1–30.0 wt %, but more preferably 1.0–10.0 wt %, relative to the total weight of cosmetic material.

The component h) is a silicone resin such as an acrylic/silicone graft or block copolymer, or a silicone lattice compound, but is preferably an acrylic silicone resin.

It is particularly preferred that this silicone resin is an acrylic silicone resin which contains at least one species chosen from a group comprising a pyrolidone part, a long chain alkyl part, a polyoxyalkylene part and a fluoroalkyl part in the molecule. This silicone resin is preferably a silicone lattice compound. The blending proportion of the silicone resin, which is an acrylic/silicone graft or block copolymer, or a silicone lattice compound, is 1.0–10.0 wt %, and more preferably 1.0–10 wt %, relative to the total amount of cosmetic material.

The component i) is an ultraviolet defense component which in addition to the ultraviolet dispersants such as inorganic pigments and metal powders mentioned above, may also be an organic ultraviolet absorber. Specific examples are benzoic acid ester ultraviolet absorbers such as p-aminobenzoic acid, ethyl p-aminobenzoate, glyceryl p-aminobenzoate, amyl p-diaminomethyl aminobenzoate, octyl p-dimethyl aminobenzoate and ethyl 4-[N,N-di(2-hydroxy propyl)] aminobenzoate; salicylic acid ultraviolet absorbers such as methyl salicylate, salicylic acid ethylene glycol, phenyl salicylate, octyl salicylate, benzyl salicylate, p-tert-butylphenyl salicylate and homomenthyl salicylate; cinnamic acid ultraviolet absorbers such as benzyl cinnamate, 2-ethoxyethyl p-methoxycinnamate, octyl p-methoxycinnamate, and di-p-methoxycinnamic acid mono-2-ethylhexanoic acid glyceride; urocanic acid ultraviolet absorbers such as urocanic acid and ethyl urocanate; benzophenone ultraviolet absorbers such as hydroxymethoxybenzophenone, hydroxymethoxybenzophenone sulfonate, sodium hydroxymethoxy benzophenone sulfonate, dihydroxy methoxybenzophenone, sodium dihydroxydimethoxybenzophenone sulfonate, 2,4-dihydroxybenzophenone and tetrahydroxybenzophenone; dibenzoylmethane ultraviolet absorbers such as 4-tert-butyl-4-methoxydibenzoylmethane; anthranilic acid ultraviolet absorbers such as menthyl anthranilate, and benzotriazol derivatives such as 2-(2-hydroxy-5-methyl phenyl) benzotriazol, and polymer derivatives, silane, or siloxane derivatives of these molecules.

The blending proportion of these ultraviolet absorbers is preferably 0.1–20.0 wt % but more preferably 1.0–10.0 wt % relative to the total amount of cosmetic material. Moreover, of these organic ultraviolet absorbers, 2-ethylhexyl p-methoxycinnamate and 4-t-butyl-4'-methoxydibenzoylmethane are particularly to be preferred.

It is possible to use organic ultraviolet absorbers sealed in a polymer powder, and the polymer powder may also be hollow. The average first order particle diameter of the polymer powder is preferably in the range 0.1–50 µm, and the particle size distribution may be broad or sharp. The type of polymer may be an acrylic resin, methacrylic resin, styrene resin, urethane resin, polyethylene resin, polypropylene resin, polyethylene terephthalate resin, silicone resin, Nylon or acrylamide resin. It is preferred that these polymer powders incorporate an organic ultraviolet absorber in a weight range of 0.1–30.0 wt % of the weight of powder, and it is particularly preferred to blend in 4-t-butyl-4'-methoxydibenzoylmethane which is a UVA absorber.

To the extent that they do not impair the effect of this invention, the components usually used in cosmetic materials may also be used in the cosmetic material of this invention, such as skin-forming agents, oil-soluble gelatinizers, organic-modified clay minerals, resins, ultraviolet absorbers, moisturizers, preservatives, antiseptics, antibacterials, perfumes, salts, antioxidants, pH regulators, chelating agents, refrigerants, anti-inflammatory agents, skin beautifying agents (whiteners, cell activators, dry and rough skin improvement agents, blood circulation promoters, skin astringents and anti-sebarrhoica agents), vitamins, aminoacids, nucleic acids, hormones and clathrates.

Examples of oil-soluble gelatinizers are metal soaps such as aluminium stearate, magnesium stearate and zinc myristate, aminoacid derivatives such as N-lauroyl-L-glutamic acid and alpha, gamma-di-n-butylamine, dextrin fatty acid esters such as dextrin palmitic acid ester, dextrin stearic acid ester and dextrin 2-ethyl hexanoic acid palmitic acid ester, cane sugar fatty acid esters such as cane sugar palmitic acid ester and cane sugar stearic acid ester, benzylidene derivatives of sorbitol such as monobenzylidene sorbitol and dibenzylidene sorbitol, and organic-modified clay minerals such as dimethylbenzyldodecylammonium montmorillonite clay and dimethyl dioctadecylammonium montmorillonite clay, one, two or more of these agents being used as necessary.

Examples of moisturizers are glycerol, sorbitol, propylene glycol, dipropylene glycol, 1,3-butylene glycol, glucose, xylitol, maltitol, polyethylene glycol, hyaluronic acid, chondroitin sulfate, pyrolidone carboxylate, polyoxyethylene methyl glucoside and polyoxypropylene methyl glucoside.

Examples of antiseptics and preservatives are paraoxybenzoic acid alkyl ester, benzoic acid, sodium benzoate, sorbic acid, potassium sorbate and phenoxyethanol; examples of antibacterials are benzoic acid, salicylic acid, carbolic acid, sorbic acid, paraoxy-benzoic acid alkyl ester, parachloro meta-cresol, hexachlorophene, benzalkonium chloride, chlorohexidine chloride, trichloro-carbanilide, photosensitizers and phenoxyethanol.

Examples of antioxidants are tocopherol, butylated hydroxyanisole, dibutylhydroxytoluene and phytic acid; examples of pH regulators are lactic acid, citric acid, glycolic acid, succinic acid, tartaric acid, dl-malic acid, potassium carbonate, sodium bicarbonate and ammonium bicarbonate; examples of chelating agents are alanine, ethylene diamine tetraacetic acid sodium salt, sodium polyphosphate, sodium metaphosphate and phosphoric acid; examples of refrigerants are L-menthol and camphor; examples of anti-inflammatory agents are allantoin, glycylrrhzin and its salts, glycyrrhetinic acid and glycyrrhetinic acid stearyl ester, tranexamic acid and azulene.

Skin beautifier components are whiteners such as placenta extract, arbutin, glutathione and creeping saxifrage extract; cell activators such as royal jelly, photosensitizers, cholesterol derivatives, and calf's blood extract; dry, rough skin improvement agents; blood circulation promoters such as nonyl acid warenylamide, nicotinic acid benzyl ester, nicotinic acid beta-butoxyethyl ester, capsaicin, zingerone, cantharis tincture, ichthammol, caffeine, tannic acid, alpha, borneol, nicotinic acid tocopherol, inositol hexanicotinate, cyclandelate, cinnarizine, tolazoline, acetylcholine, verapamil, cepharanthin and gamma-orizanol, skin astringents such as zinc oxide and tannic acid, and anti-sebarrhoica agents such as sulfur and thianthol.

Examples of vitamins are vitamin A such as vitamin A oil, retinol, retinal acetate and retinal palmitate; vitamin B, i.e, vitamin B2 such as riboflavin, riboflavin butyrate, flavin adenine nucleotide; vitamin B6 such as pyridoxine hydrochloride, pyridoxine dioctanoate and pyridoxine tripalmitate; vitamin B12 and its derivatives, and vitamin B15 and its derivatives; vitamin C such as L-ascorbic acid, L-ascorbic acid dipalmitic acid ester, L-ascorbic acid-2-sodium sulfate and dipotassium L-ascorbic acid phosphoric acid diester; vitamin D such as ergocalciferol and cholecalciferol; vitamin E such as alpha-tocopherol, beta-tocopherol, gamma-tocopherol, acetic acid dl-alpha-tocopherol, nicotinic acid dl-alpha-tocopherol and succinic acid dl-alpha-tocopherol; vitamin H, vitamin P, nicotinic acids such as nicotinic acid, benzyl nicotinate and nicotinamide, pantothenic acids such as calcium pantothenate, D-pantothenyl alcohol, pantothenyl ethyl ether and acetyl pantothenyl ethyl ether, and biotin.

Examples of amino acids are glycine, valine, leucine, isoleucine, serine, threonine, phenylalanine, arginine, lysine, aspartic acid, glutamic acid, cystine, cysteine, methionine and tryptophan; examples of nucleic acids are deoxyribonucleic acid; and examples of hormones are estradiol and ethenyl estradiol.

Examples of astringent components are aluminium chlorohydrate and aluminium zirconium chlorohydrate, specific examples being Microdry UIF, REACH 101, REACH REACH 103, REACH 301, REACH 301 solution, REACH 501, REACH 501 solution, REHYDROL II, REACH AZP 902, REACH AZP 908, REACH AZP 855, REACH AZZ 902, REACH AZZ 855, REACH AZN 885, REZAL 36P, REZAL 36P solution, REZAL 36GP, REZAL 36G solution, REZAL 67P and REZAL 67 solution (product of REHEIS Co.).

There is no particular limitation on the applications of the cosmetic material of this invention, i.e., skincare products, hair products, antiperspirant products, makeup products, ultraviolet protection products and perfume solvents. Specific examples are basic cosmetic materials such as emulsions, creams, lotions, calamine lotion, sunscreens, sun tan agents, aftershave lotion, preshave lotion, packs, cleansing materials, face washing materials, anti-acne cosmetic materials and essences; makeup materials such as foundations, white powders, eye shadow, eyeliners, eye blow, cheek, lipstick and nail colors; and shampoos, rinses, conditioners, haircare, hair tonics, setting agents, body powders, deodorants, depilation agents, soaps, body shampoos, bath salts, hand soaps and perfumes. There is no particular limitation on the form of the product, which may be a liquid, emulsion, cream, solid, paste, gel, powder, laminate, mousse or spray.

Advantages of the Invention

The silicone polymer of this invention has water repellence, oil repellence, swells up relative to fluorine-modified silicone oils having a high fluorine-substituted alkyl group content, and forms a homogeneous paste-like composition. Further, cosmetic materials with which this composition is blended allow stable dispersion of fluorine-modified silicone oils, do not easily separate and feel very clean to use. Even when water is blended to form an emulsion, the target emulsion can easily be obtained, and a cosmetic material wherefrom water does not separate on storage and which has excellent stability can be obtained.

EXAMPLES

This invention will now be described in more detail referring to specific examples, but the invention is not be construed as being limited thereby. Viscosities are given at 25 degree C. % units refer to wt %.

Example 1

118 weight parts of the organohydrogen polysiloxane having the following average empirical formula (1)

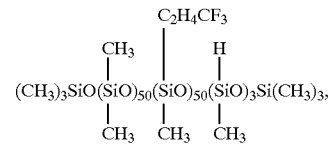

and 175 weight parts of the organopolysiloxane having the following average empirical formula (2)

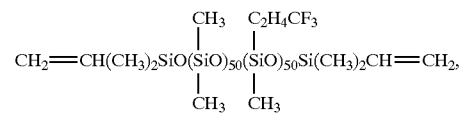

were introduced into a reactor, 0.1 wt % of a divinyltetramethyl siloxane solution of 2 wt % chloroplatinic acid was added, and the reaction mixture was stirred for 2 hours while maintaining the internal temperature and 70–80 degree C. An elastic silicone polymer was obtained.

Example 2

82 weight parts of the organohydrogen polysiloxane having the following average empirical formula (3)

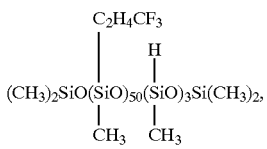

and 12 weight parts of the organopolysiloxane having the following average empirical formula (4)

$$CH_2=CHCH_2O(C_2H_4O)_{15}CH_2CH=CH_2,$$

were introduced into a reactor, 0.02 wt % of a divinyltetramethyl siloxane solution of 2 wt % chloroplatinic acid was added, and the reaction mixture was stirred for 2 hours while maintaining the internal temperature and 70–80 degree C. An elastic silicone polymer was obtained.

Comparative Example 1

486 weight parts of the organohydrogen polysiloxane having the following average empirical formula (5)

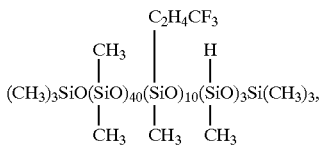

and 72 and and and weight parts of the organopolysiloxane having the following average empirical formula (6)

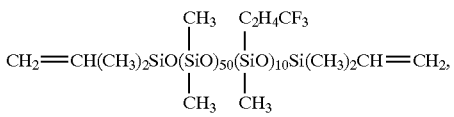

were introduced into a reactor, 0.1 wt % of a divinyltetramethyl siloxane solution of 2 wt % chloroplatinic acid was added, and the reaction mixture was stirred for 2 hours while maintaining the internal temperature and 70–80 degree C. An elastic silicone polymer was obtained.

Comparative Example 2

486 weight parts of the organohydrogen polysiloxane having the above average empirical formula (5), and 115 weight parts of the organopolysiloxane having the above average empirical formula (4), were introduced into a reactor, 0.05 wt % of a divinyltetramethyl siloxane solution of 2 wt % chloroplatinic acid was added, and the reaction mixture was stirred for 2 hours while maintaining the internal temperature and 70–80 degree C. An elastic silicone polymer was obtained.
Solubility of Silicone Polymer, and Swelling Properties of Penta-3,3,3-trifluoropropyl pentamethylcyclopentas 10 wt parts of the polymer obtained were mixed with 90 weight parts of an organic solvent shown in Table 1, and the solubility after stirring for 2 hours was examined. The amount of penta-3,3,3-trifluoropropyl pentamethyl cyclopentasiloxane which could be contained is shown in Table 2.

Herein, the amount of penta-3,3,3-trifluoropropyl pentamethyl cyclopentasiloxane which can be contained was measured by the following method.

Firstly, a fixed amount of the silicone polymer was taken in a vessel, penta-3,3,3-trifluoropropyl pentamethyl cyclopentasiloxane was added, and the mixture left at room temperature without stirring for 10 hours. After leaving, the sample was placed on a 100 mesh net, and it was examined whether or not penta-3,3,3-trifluoropropyl pentamethyl cyclopentasiloxane had separated. The measurement criterion was that the amount of penta-3,3,3-trifluoropropyl pentamethyl cyclopentasiloxane which separated after leaving for five minutes was less than 10%. When the separation amount was less than 10%, confirmation tests were performed by adding more penta-3,3,3-trifluoropropyl pentamethyl cyclopentasiloxane until the separation amount was at least 10%.

TABLE 1

Solubility of silicone polymer

| | | Example 1 | Example 2 | Comparative example 1 | Comparative example 2 |
|---|---|---|---|---|---|
| Solubility | 2-propanol | Does not dissolve | Does not dissolve | Does not dissolve | Does not dissolve |
| | Toluene | Does not dissolve | Does not dissolve | Does not dissolve | Does not dissolve |
| | Acetone | Does not dissolve | Does not dissolve | Does not dissolve | Does not dissolve |
| | Carbon tetrachloride | Does not dissolve | Does not dissolve | Does not dissolve | Does not dissolve |
| Amount of penta-3,3,3-trifluoropropyl pentamethyl cyclopentasiloxane* | | 250 | 200 | 10 | 5 |

*Amount (weight parts) that can be contained in 100 weight parts of silicone polymer From the above results, it is seen that, as the silicone polymers of the comparative examples also have a three-dimensional crosslinked structure, they are insoluble in organic solvents, but they do not have swelling properties relative to fluorine-modified silicone oils having a high fluoroalkyl group content, i.e., a high water repellence and oil repellence. On the other hand, the silicone polymer of this invention is insoluble in organic solvents, and does have excellent swelling properties relative to high fluorine-modified silicone oils.

Example 3

20 wt parts of the silicone polymer of Example 1 were mixed with 80 wt parts of tetra-3,3,3-trifluoropropyl pentamethyl cyclopentasiloxane/penta-3,3,3-trifluoropropyl pentamethyl cyclopentasiloxane mixture (1/1 weight ratio, viscosity 60 m2/s), and the mixture thoroughly kneaded in a three roller roll mill. A semi-transparent paste-like composition having thixotropic properties was obtained. Even after leaving this paste-like composition at 50 degree C. for one month, no separation of the oil component was observed.

Comparative Example 3

20 wt parts of the silicone polymer of Comparative Example 1 were mixed with 80 wt parts of tetra-3,3,3-trifluoropropyl pentamethyl cyclopentasiloxane/penta-3,3,3-trifluoropropyl pentamethyl cyclopentasiloxane mixture (1/1 weight ratio, viscosity 60 m2/s), and the mixture was thoroughly kneaded in a three roller roll mill. A homogeneous composition could not be obtained.

Example 4

30 wt parts of the silicone polymer of Example 2 were mixed with 70 wt parts of the fluorine-modified silicone oil (100 mm²/s) represented by the following average empirical formula (7)

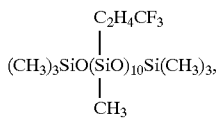
$$(CH_3)_3SiO(SiO)_{10}Si(CH_3)_3,$$
with $C_2H_4CF_3$ and $CH_3$ substituents and the mixture was thoroughly kneaded in a three roller roll mill. A semi-transparent paste-like composition having thixotropic properties was obtained. Even after leaving this paste-like composition at 50 degree C for one month, no separation of the oil component was observed.

When 50 weight parts of water were gradually added to 50 weight parts of this paste-like composition with stirring, a W/O emulsion was formed without the addition of an emulsifying agent. Even after leaving this emulsion at 50 degree C. for one month, no separation of the oil component was observed.

Comparative Example 30 wt parts of the silicone polymer of Comparative Example 2 were mixed with 70 wt parts of the fluorine-modified silicone oil (100 mm²/s) represented by the above average empirical formula (7), and the mixture was thoroughly kneaded in a three roller roll mill. A homogeneous composition could not be obtained.

Example 5

567 weight parts of the organohydrogen polysiloxane having the following average empirical formula (8)

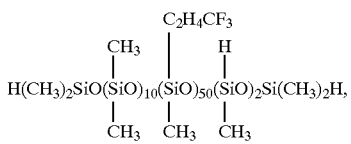

and 955 weight parts of the organopolysiloxane having the following average empirical formula (9)

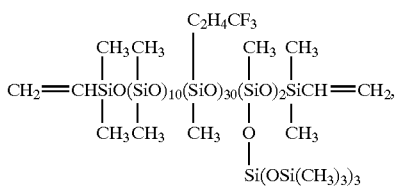

were introduced into a reactor, 0.1 wt % of a divinyltetramethyl siloxane solution of 2 wt % chloroplatinic acid was added, and the reaction mixture was stirred for 2 hours while maintaining the internal temperature at 70–80 degree C. An elastic silicone polymer was obtained.

30 wt parts of this silicone polymer were mixed with 70 wt parts of with the fluorine-modified silicone oil (viscosity 150 mm²/s) represented by the following average empirical formula (10)

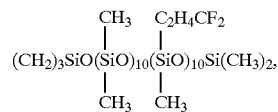

and the mixture was thoroughly kneaded in a three roller roll mill.

A semi-transparent paste-like composition having thixotropic properties was obtained. Even after leaving this paste-like composition at 50 degree C. for one month, no separation of the oil component was observed.

Example 6

622 weight parts of the organohydrogen polysiloxane having the following average empirical formula (11)

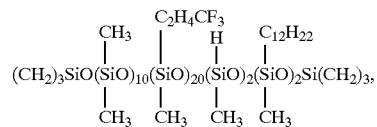

and 180 weight parts of the organopolysiloxane having the following average empirical formula (12)

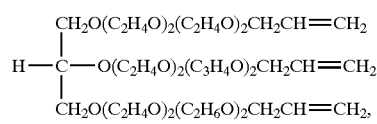

were introduced into a reactor, 0.1 wt % of a divinyltetramethyl siloxane solution of 2 wt % chloroplatinic acid was added, and the reaction mixture was stirred for 2 hours while maintaining the internal temperature at 70–80 degree C. An elastic silicone polymer was obtained.

25 wt parts of this silicone polymer were mixed with 75 wt parts of the fluorine-modified silicone oil represented by the above average empirical formula (7), and the mixture was thoroughly kneaded in a three roller roll mill. A semi-transparent paste-like composition having thixotropic properties was obtained. Even after leaving this paste-like composition at 50 degree C. for one month, no separation of the oil component was observed.

Example 7

Suntan Cream

A suntan cream was obtained using the following combination.

| (Component) | (%) |
|---|---|
| 1. Paste-like silicone composite of Example 3 | 20.0 |
| 2. Silicone wax | 0.5 |
| 3. Polyether-denatured siloxane* | 2.2 |
| 4. Polyether oleyl co-modified silicone** | 6.0 |
| 5. Palmitic acid | 0.2 |
| 6. Dimethyloctyl p-aminobenzoic acid | 0.5 |
| 7. 4-t-butyl-4'-methoxy-dibenzoylmethane | 0.5 |
| 8. Kaolin | 0.5 |
| 9. Red ocher | 0.2 |
| 10. Yellow iron oxide | 0.3 |
| 11. Black iron oxide | 0.1 |
| 12. Titanium oxide-coated mica | 1.0 |

| (Component) | (%) |
|---|---|
| 13. L-sodium glutamate | 3.0 |
| 14. 1,3-butylene glycol | 5.0 |
| 15. Dioctadecyldimethyl ammonium chloride | 0.1 |
| 16. Antioxidants | Suitable amount |
| 17. Preservative | Suitable amount |
| 18. Perfume | Suitable amount |
| 19. Purified water | Suitable amount |

*FPD-4694 (Shin-Etsu Chemical Co., Ltd.)
**KF-6026 (Shin-Etsu Chemical Co., Ltd.)

It was found that the sun tan cream obtained above had a fine texture, spread easily, was not sticky or oily, and had a moist, fresh, clean feel when used. It had excellent compatibility with the skin, lasted well, showed no change such as separation or powder agglomeration with temperature or time, and was very stable.

Example 8
Foundation

A foundation was obtained using the following combination.

| (Component) | (%) |
|---|---|
| 1. Paste-like silicone composite of Example 4 | 45.0 |
| 2. Fluorine-modified silicone (fluorine group content 40 mol %, viscosity 100 cs) | 5.0 |
| 3. Octadecyldimethylbenzyl ammonium salt-modified montmorillonite | 4.0 |
| 4. Hydrophobically-treated titanium oxide*** | 10.0 |
| 5. Hydrophobically-treated talc*** | 6.0 |
| 6. Hydrophobically-treated mica*** | 6.0 |
| 7. Hydrophobically-treated red ocher*** | 1.6 |
| 8. Hydrophobically-treated yellow iron oxide*** | 0.7 |
| 9. Hydrophobically-treated black iron oxide*** | 0.2 |
| 10. Dipropylene glycol | 5.0 |
| 11. p-oxybenzoic acid methyl ester | 0.3 |
| 12. 2-amino-2-methyl-1,3-propanediol | 0.2 |
| 13. Hydrochloric acid | 0.1 |
| 14. Perfume | Suitable amount |
| 15. Water | Remainder |

***Hydrophobic Treatment: Heat treatment after adding 2% methylhydrogenpolysiloxane to the powder.

It was found that the foundation obtained above had a fine texture, spread easily without being sticky or oily, was moist and fresh, and had a clean feel when used. It also lasted well, did not change with temperature or time, and was very stable.

Example 9
Hair Cream

A hair cream was obtained using the following combination.

| (Component) | (%) |
|---|---|
| 1. Paste-like silicone composite of Example 5 | 10.0 |
| 2. Methylphenyl polysiloxane | 5.0 |
| 3. Squalane | 4.0 |
| 4. Silicone resin | 1.0 |
| 5. Dioleic acid glyceride | 2.0 |
| 6. Polyether-modified siloxane* | 2.0 |
| 7. Polyether oleyl-modified silicone** | 4.0 |
| 8. Sorbitol sodium sulfate | 2.0 |

| (Component) | (%) |
|---|---|
| 9. Sodium chondroitin sulfate | 1.0 |
| 10. Sodium hyaluronate | 0.5 |
| 11. Propylene glycol | 3.0 |
| 12. Preservative | 1.5 |
| 13. Vitamin E acetate | 0.1 |
| 14. Antioxidant | Suitable amount |
| 15. Perfume | Suitable amount |
| 16. Purified water | Suitable amount |

*FPD-4694 (Shin-Etsu Chemical Co., Ltd.)
**KF-6026 (Shin-Etsu Chemical Co., Ltd.)

It was found that the hair cream obtained above spread easily, was not sticky or oily, and had a moist, fresh, clean feel when used. It had excellent water-resistance, water repellence and good anti-perspirant properties, and lasted well. It did not change with temperature or time, and was very stable.

Example 10
Mascara

| (Component) | (%) |
|---|---|
| 1. Acrylic silicone resin* | 20.0 |
| 2. Palmitic acid/dextrin ethyl hexanoate | 8.0 |
| 3. Polyethylene wax | 4.0 |
| 4. Bees wax | 7.0 |
| 5. Lecithin | 0.5 |
| 6. Paste-like silicone composite of Example 6 | 22.0 |
| 7. C11–12 liquid isoparaffin | 20.0 |
| 8. Iron oxide | 5.0 |
| 9. Silicic acid anhydride | 3.5 |
| 10. Talc | 10.0 |

*acrylic silicone resin; KP-545 (Shin-Etsu Chemical Co., Ltd.)

It was found that the mascara obtained above spread easily, was not sticky or oily, and had a moist, fresh, clean feel when used. It had excellent water-resistance, water repellence and good anti-perspirant properties, and lasted well. It did not change with temperature or time, and was very stable.

Example 11
Cream

A cream was obtained using the following combination.

| (Component) | (%) |
|---|---|
| 1. Paste-like silicone composite of Example 3 | 20.0 |
| 2. Trioctanoic acid glyceride | 10.0 |
| 3. Polyether-modified siloxane* | 1.5 |
| 4. Polyether-modified siloxane** | 4.0 |
| 5. Phenyldimethylstearylammonium chloride | 1.0 |
| 6. Zypropyrene glycol | 10.0 |
| 7. Maltitol | 10.0 |
| 8. Saponite | 1.5 |
| 9. Preservative | Suitable amount |
| 10. Perfume | Suitable amount |
| 11. Purified water | Remainder |

*KF-6017 (Shin-Etsu Chemical Co., Ltd.)
**FPD-4694 (Shin-Etsu Chemical Co., Ltd.)

It was found that the cream obtained above spread easily, was not sticky or oily, and had a moist, fresh, clean feel when used. It had excellent water-resistance and water repellence, and lasted well. It did not change with temperature or time, and was very stable.

Example 12

Hand Cream

A cream was obtained using the following combination.

| (Component) | (%) |
|---|---|
| 1. Paste-like silicone composite of Example 4 | 12.0 |
| 2. Liquid paraffin | 10.0 |
| 3. Organic silicone resin* | 5.0 |
| 4. Polyether-modified siloxane** | 1.9 |
| 5. Distearyldimethylammonium chloride | 0.8 |
| 6. Vitamin E acetate | 0.1 |
| 7. Polyethylene glycol 4000 | 1.0 |
| 8. Glycerol | 10.0 |
| 9. Sumectone | 1.2 |
| 10. Preservative | Suitable amount |
| 12. Perfume | Suitable amount |
| 13. Purified water | Remainder |

*organic silicone resin; average formula (CH3)1.60SiO1.20, molecular weight 3,000
**KF-6017 (Shin-Etsu Chemical Co., Ltd.)

It was found that the hand cream obtained above spread easily, was not sticky or oily, and had a moist, fresh, clean feel when used. It had excellent water-resistance and water repellence, and lasted well. It did not change with temperature or time, and was very stable.

Example 13

Sunscreen Cream

A sunscreen cream was obtained using the following combination.

| (Component) | (%) |
|---|---|
| 1. Paste-like silicone composition of Example 5 | 20.0 |
| 2. Liquid paraffin | 10.0 |
| 3. Polyether-modified siloxane* | 1.9 |
| 4. Polyether oleyl modified silicone** | 4.0 |
| 5. 4-t-butyl-4'-methoxydibenzoylmethane | 7.0 |
| 6. Distearyldimethylammonium chloride | 0.8 |
| 7. Vitamin E acetate | 0.1 |
| 8. Ethanol | 1.0 |
| 9. Sumectone | 1.2 |
| 10. Preservative | Suitable amount |
| 11. Perfume | Suitable amount |
| 12. Purified water | Remainder |

*KF-6017 (Shin-Etsu Chemical Co., Ltd.)
**KF-6026 (Shin-Etsu Chemical Co., Ltd.)

It was found that the sunscreen cream obtained above had a fine texture, spread easily and had a moist, fresh feel. It was not sticky so sand did not stick to it at all, and it was very easy to use. It was also found to last well, and its ultraviolet protection effect continued for a long time. Also, it did not change with temperature or time, and was very stable.

Example 14

Cream

A cream was obtained using the following combination.

| (Component) | (%) |
|---|---|
| 1. Paste-like silicone composite of Example 6 | 10.0 |
| 2. Dimethyl polysiloxane (6 cs) | 5.0 |
| 3. Liquid paraffin | 5.0 |
| 4. Polyether-modified siloxane* | 3.0 |
| 5. Polyether oleyl-modified silicone** | 5.0 |
| 6. Sodium citrate | 2.0 |
| 7. 1,3-butylene glycol | 5.0 |
| 8. Preservative | Suitable amount |
| 9. Perfume | Suitable amount |
| 10. Purified water | Remainder |

*KF-6017 (Shin-Etsu Chemical Co., Ltd.)
**SPD-4694 (Shin-Etsu Chemical Co., Ltd.)

It was found that the cream obtained above spread easily, was not sticky or oily, and had a moist, fresh, clean feel when used. It had excellent water-resistance and water repellence, and lasted well. It did not change with temperature or time, and was very stable.

Example 15

Eye Shadow

An eye shadow was obtained using the following combination.

| (Component) | (%) |
|---|---|
| 1. Paste-like silicone composite of Example 3 | 15.0 |
| 2. Dimethyl polysiloxane (6 cs) | 10.0 |
| 3. Polyether modified silicone* | 2.0 |
| 4. PEG(10) lauryl ether | 0.5 |
| 5. Silicone-treated chrome oxide** | 6.2 |
| 6. Silicone-treated ultramarine blue** | 4.0 |
| 7. Silicone-treated titanium-coated mica** | 6.0 |
| 8. Sodium chloride | 2.0 |
| 9. Propylene glycol | 8.0 |
| 10. Preservative | Suitable amount |
| 11. Perfume | Suitable amount |
| 12. Purified water | Remainder |

*FPD-6131 (Shin-Etsu Chemical Co., Ltd.)
**Silicone treatment: Heat treatment after adding 3% of hydrogen polysiloxane to powder It was found that the eye shadow obtained above spread easily, was not oily or powdery, and had a fresh, clean feel when used. It also had good water-resistance, water repellence and antiperspirant properties, lasted well and did not easily fall off. It did not change with temperature or time, and was very stable.

Example 16

Eyeliner

An eyeliner was obtained using the following combination.

| (Component) | (%) |
|---|---|
| 1. Paste-like silicone composite of Example 4 | 22.0 |
| 2. Dimethyl polysiloxane (6 cs) | 5.0 |
| 3. Jojoba oil | 2.0 |
| 4. Polyether-modified silicone* | 1.0 |
| 5. Silicone-treated black iron oxide** | 20.0 |
| 6. Ethanol | 5.0 |
| 7. Preservative | Suitable amount |
| 8. Purified water | Remainder |

*KF-6017 (Shin-Etsu Chemical Co., Ltd.)
**silicone-treated black iron oxide: heat treatment after adding 2% of methylhydrogen polysiloxane to black iron oxide.

It was found that the eyeliner obtained above spread easily, was not oily or powdery, and had a fresh, clean feel when used. It also had good water-resistance, water repellence and antiperspirant properties, lasted well and did not easily fall off. It did not change with temperature or time, and was very stable.

Example 17
Lip Cream

A lip cream was obtained using the following combination.

| (Component) | (%) |
|---|---|
| 1. Paste-like silicone composite of Example 6 | 40.0 |
| 2. Isoparaffin (boiling point 155 degree C) | 10.0 |
| 3. Squalane | 10.0 |
| 4. Lanolin | 2.0 |
| 5. Trimethylsiloxy silicate | 3.0 |
| 6. Microcrystalline wax | 3.0 |
| 7. Polyether-modified silicone* | 3.0 |
| 8. L-glutamic acid dibutylamide | 5.0 |
| 9. Sodium lactate | 0.3 |
| 10. L-sodium glutamate | 0.3 |
| 11. Sodium hyaluronate | 0.1 |
| 12. Sorbitol | 0.5 |
| 13. Glycerol | 5.0 |
| 14. Red No. 202 | Suitable amount |
| 15. Menthol | Suitable amount |
| 16. Preservative | Suitable amount |
| 17. Perfume | Suitable amount |
| 18. Purified water | Remainder |

*KF-6017 (Shin-Etsu Chemical Co., Ltd.)

It was found that the solid W/O lip cream obtained above spread easily, was not sticky or oily, and had a moist, fresh, clean feel when used. It also lasted well, had a good treatment effect, did not change with temperature or time, and was very stable.

Example 18
Liquid Emulsion Foundation

Liquid emulsion foundation was obtained using the following combination.

| (Component) | (%) |
|---|---|
| 1. Decamethylcyclopentasiloxane | 5.0 |
| 2. Paste-like silicone composite of Example 5 | 15.0 |
| 3. Squalane | 4.0 |
| 4. Dioctanoic acid neopentyl glycol | 3.0 |
| 5. Myristic acid isostearic acid diglyceride | 2.0 |
| 6. Alpha-monoisostearyl glyceryl ether | 1.0 |
| 7. Polyether-modified silicone* | 1.0 |
| 8. Aluminum distearate | 0.2 |
| 9. Hydrophobically-treated titanium oxide** | 5.0 |
| 10. Hydrophobically-treated sericite** | 2.0 |
| 11. Hydrophobically-treated talc** | 3.0 |
| 12. Hydrophobically-treated red ocher** | 0.4 |
| 13. Hydrophobically-treated yellow iron oxide** | 0.7 |
| 14. Hydrophobically-treated black iron oxide** | 0.1 |
| 15. Magnesium sulfate | 0.7 |
| 16. Glycerol | 3.0 |
| 17. Preservative | Suitable amount |
| 18. Perfume | Suitable amount |
| 19. Purified water | Remainder |

*KF-6015 (Shin-Etsu Chemical Co., Ltd.)
**Hydrophobically-treated powder: 2% of stearic acid was added to the powder It was found that the liquid emulsion obtained above had a low viscosity, spread easily, was not sticky or oily, and had a moist, fresh, clean feel when used. It also lasted well, did not change with temperature or time, and was very stable.

Example 19
Sweating Inhibitor

A sweating inhibitor was obtained using the following combination.

| (Component) | (%) |
|---|---|
| 1. Paste-like silicone composite of Example 3 | 30.0 |
| 2. Polyether oleyl-modified silicone* | 1.0 |
| 3. Mono-oleic acid polyoxyethylene sorbitan (20 E.O.) | 0.5 |
| 4. Glycine salt of aluminium zirconium hydrate tetrachloride | 20.0 |
| 5. Purified water | Remainder |

*FPD-4694 (Shin-Etsu Chemical Co., Ltd.)

It was found that the sweating inhibitor obtained above spread easily, was not sticky or oily, did not whiten too much and had a clean feel when used. It did not change with temperature or time, and was very stable.

Example 20
Transparent Gel Cosmetic Material

A transparent gel cosmetic material was obtained using the following combination.

| (Component) | (%) |
|---|---|
| 1. Paste-like silicone composite of Example 4 | 10.0 |
| 2. Polyether-modified silicone* | 10.0 |
| 3. 1,3-butylene glycol | 10.0 |
| 4. Polyethylene glycol 400 | 9.0 |
| 5. 2-hydroxy octanoate | 1.0 |
| 6. Sorbitol (70% aqueous solution) | 10.0 |
| 7. Citric acid | Suitable amount |
| 8. Sodium citrate | Suitable amount |
| 9. Preservative | Suitable amount |
| 10. Perfume | Suitable amount |
| 11. Purified water | Remainder |

*FPD-4668 (Shin-Etsu Chemical Co., Ltd.)

It was found that the transparent gel cosmetic material obtained spread easily, was not sticky or oily; and had a moist, fresh, clean feel when used. It was also highly compatible with the skin, did not change with temperature or time, and was very stable

Example 21
Sunscreen Toilet Water

A sunscreen toilet water was obtained using the following combination.

| (Component) | (%) |
|---|---|
| 1. Paste-like silicone composite of Example 6 | 14.0 |
| 2. Polyether-modified silicone* | 10.0 |
| 3. Squalane | 1.5 |
| 4. octyl p-methoxy cinnamate | 3.0 |
| 5. Hydrophobically-treated ultrafine titanium oxide** | 2.0 |
| 6. 1,3-butylene glycol | 10.0 |
| 7. Sodium chloride | 2.0 |
| 8. L-proline | 0.1 |
| 9. 2-hydroxyoctanoic acid | 1.0 |
| 10. 2-hydroxypropanoic acid | 5.0 |
| 11. Sodium hydroxide | Suitable amount |
| 12. Preservative | Suitable amount |
| 13. Perfume | Suitable amount |
| 14. Purified water | Remainder |

*KF-615A (Shin-Etsu Chemical Co., Ltd.)
**Hydrophobically-treated ultrafine titanium oxide: titanium TTO-S2 (Sakai Chemical Co.)

It was found that the sunscreen toilet water obtained spread easily, was not sticky or oily, and had a moist, fresh, clean feel when used. It was also highly compatible with the skin, had excellent sunscreen properties, did not change with temperature or time, and was very stable.

Example 22
Cream

A cream was obtained using the following combination.

| (Component) | (%) |
|---|---|
| 1. Paste-like silicone composite of Example 3 | 20.0 |
| 2. Liquid paraffin | 5.0 |
| 3. Polyether-modified silicone* | 1.0 |
| 4. L-ascorbic acid magnesium phosphate | 3.0 |
| 5. Dipropylene glycol | 5.0 |
| 6. Glycerol | 5.0 |
| 7. Preservative | Suitable amount |
| 8. Perfume | Suitable amount |
| 9. Purified water | Remainder |

*KF-615A (Shin-Etsu Chemical Co., Ltd.)

It was found that the cream obtained had a fine texture, spread easily, was not sticky or oily, and had a moist, fresh, clean feel when used.- It was also highly compatible with the skin, had an excellent whitening effect, did not change with temperature or time, and was very stable.

Example 23
Milky Lotion

A milky lotion was obtained using the following combination.

| (Component) | (%) |
|---|---|
| 1. Paste-like silicone composite of Example 4 | 18.0 |
| 2. Dimethyl polysiloxane (6 cs) | 6.0 |
| 3. Squalane | 5.0 |
| 4. Dioctanoic acid neopentyl glycol | 3.0 |
| 5. Alpha-mono-oleyl glyceryl ether | 1.0 |
| 6. Polyether-modified silicone* | 2.0 |
| 7. Aluminum distearate | 0.2 |
| 8. Magnesium sulfate | 0.7 |
| 9. Glycerol | 5.0 |
| 10. Preservative | Suitable amount |
| 11. Perfume | Suitable amount |
| 12. Purified water | Remainder |

*KF-6017 (Shin-Etsu Chemical Co., Ltd.)

It was found that the liquid emulsion obtained above had a low viscosity, spread easily, was not sticky or oily, and had a moist, fresh, clean feel when used. It also lasted well, did not change with temperature or time, and was very stable.

Example 24
Milky Lotion

A milky lotion was obtained using the following combination.

| (Component) | (%) |
|---|---|
| 1. Paste-like silicone composite of Example 5 | 15.0 |
| 2. Dimethylpolysiloxane (6 cs) | 6.0 |
| 3. Squalane | 5.0 |
| 4. Dioctanoic acid neopentyl glycol | 3.0 |
| 5. Alpha-mono-oleyl glyceryl ether | 1.0 |
| 6. Polyether oleyl-modified silicone* | 1.5 |
| 7. Polyether-modified silicone** | 1.0 |
| 8. Aluminium distearate | 0.2 |
| 9. Dextrin fatty acid ester | 1.0 |
| 10. Magnesium sulfate | 0.7 |
| 11. Glycerol | 5.0 |
| 12. Preservative | Suitable amount |
| 13. Perfume | Suitable amount |
| 14. Purified water | Remainder |

*KF6026 (Shin-Etsu Chemical Co., Ltd.)
**KF-6017 (Shin-Etsu Chemical Co., Ltd.)

It was found that the liquid emulsion obtained above had a low viscosity, spread easily, was not sticky or oily, and had a moist, fresh, clean feel when used. It also lasted well, did not change with temperature or time, and was very stable.

Example 25
Sunscreen Cream

A sunscreen cream was obtained using the following combination.

| (Component) | (%) |
|---|---|
| 1. Paste-like silicone composite of Example 6 | 18.0 |
| 2. Methylphenyl polysiloxane | 2.0 |
| 3. Liquid paraffin | 1.5 |
| 4. Polyether-modified silicone* | 4.0 |
| 5. Octyl p-methoxy cinnamate | 5.0 |
| 6. 1,3-butylene glycol | 4.0 |
| 7. Sodium chloride | 1.0 |
| 8. Preservative | Suitable amount |
| 9. Perfume | Suitable amount |
| 10. Purified water | Remainder |

*KF-6012 (Shin-Etsu Chemical Co., Ltd.)

It was found that the sunscreen cream obtained above had a fine texture, spread easily and had a moist, fresh feel. It was not oily or sticky, and was very easy to use. It had excellent water resistance and antiperspirant properties, lasted well and its ultraviolet protection effect continued for a long time. Also, it did not change with temperature or time, and was very stable.

Example 26
Cream

A cream was obtained using the following combination.

| (Component) | (%) |
|---|---|
| 1. Paste-like silicone composite of Example 3 | 20.0 |
| 2. Methylphenyl polysiloxane | 5.0 |
| 3. Polyether-modified silicone* | 1.0 |
| 4. Dextrin fatty acid ester | 1.0 |
| 5. Glycerol | 5.0 |
| 6. Sodium chloride | 1.0 |
| 7. Preservative | Suitable amount |
| 8. Perfume | Suitable amount |
| 9. Purified water | Remainder |

*KF-6012 (Shin-Etsu Chemical Co., Ltd.)

It was found that the sunscreen cream obtained above had a fine texture, spread easily and had a moist, fresh feel. It was not oily or sticky, and was very easy to use. It had excellent water resistance and antiperspirant properties, lasted well and its ultraviolet protection effect continued for a long time. Also, it did not change with temperature or time, and was very stable.

Example 27

Foundation

A foundation was obtained using the following combination.

| (Component) | (%) |
| --- | --- |
| 1. Paste-like silicone composite of Example 4 | 18.0 |
| 2. Methylphenyl polysiloxane | 5.0 |
| 3. Monoisostearic acid sorbitan | 0.5 |
| 4. Monoisostearic acid diglyceride | 0.5 |
| 5. Polyether-modified silicone* | 1.0 |
| 6. Octyl p-methoxycinnamate | 3.0 |
| 7. Titanium oxide | 10.0 |
| 8. Red ocher | 0.13 |
| 9. Yellow iron oxide | 0.3 |
| 10. Black iron oxide | 0.07 |
| 11. Talc | 2.5 |
| 12. Sorbitol | 2.0 |
| 13. Magnesium sulfate | 0.1 |
| 14. Ethanol | 10.0 |
| 15. Preservative | Suitable amount |
| 16. Perfume | Suitable amount |
| 17. Purified water | Remainder |

*KF-6012 (Shin-Etsu Chemical Co., Ltd.)

It was found that the foundation obtained above was not sticky, spread easily, and had a clean, very cool feeling. Its emulsion state was good, was not much affected by temperature, did not separate or condense with time, and was very stable.

Example 28

Liquid Foundation

A liquid foundation was obtained using the following combination.

| (Component) | (%) |
| --- | --- |
| 1. Paste-like silicone composite of Example 5 | 15.0 |
| 2. Dimethylpolysiloxane (6 cs) | 5.0 |
| 3. Liquid paraffin | 3.0 |
| 4. Polyether-modified silicone* | 3.0 |
| 5. Palmitic acid | 0.5 |
| 6. Hydrophobic silica** | 5.0 |
| 7. Titanium oxide | 6.0 |
| 8. Red ocher | 0.25 |
| 9. Yellow iron oxide | 0.6 |
| 10. Black iron oxide | 0.12 |
| 11. Sericite | 8.03 |
| 12. Dipropylene glycol | 10.0 |
| 13. Magnesium sulfate | 2.0 |
| 14. Preservative | Suitable amount |
| 15. Antioxidant | Suitable amount |
| 16. Perfume | Suitable amount |
| 17. Purified water | Remainder |

*KF6015 (Shin-Etsu Chemical Co., Ltd.)
**Hydrophobic silica; Aerogel RY200 (made by Japan Aerogel, Inc.)

It was found that the foundation obtained above was not sticky, spread easily, and had a clean, very cool feeling. Its emulsion state is good, it lasts well, it is not much affected by temperature, and it is very stable over time.

Example 29

Sunscreen Milky Lotion

A sunscreen milky lotion was obtained by the following combination.

| (Component) | (%) |
| --- | --- |
| 1. Paste-like silicone composite of Example 6 | 25.0 |
| 2. Monoisostearic acid glyceride | 1.5 |
| 3. Pentaisostearic acid glyceride | 1.5 |
| 4. Polyether-modified silicone* | 0.5 |
| 5. Olive oil | 1.0 |
| 6. Particulate titanium oxide | 7.0 |
| 7. Glycerol | 5.0 |
| 8. Sodium chloride | 1.5 |
| 9. Preservative | Suitable amount |
| 10. Perfume | Suitable amount |
| 11. Purified water | Remainder |

*KF-6012 (Shin-Etsu Chemical Co., Ltd.)

It was found that the sunscreen milky lotion obtained above had a low viscosity, spread easily, was not sticky, and had a moist, fresh, clean feel when used. It also lasted well, its ultraviolet protection effect continued for a long time, and it had excellent powder dispersion stability and emulsion stability with regard to temperature and time.

Example 30

Sunscreen Milky Lotion

A sunscreen milky lotion was obtained using the following combination.

| (Component) | (%) |
| --- | --- |
| 1. Paste-like silicone composite of Example 3 | 20.0 |
| 2. Methylphenyl polysiloxane | 3.0 |
| 3. Monoisostearic acid sorbitan | 1.0 |
| 4. Polyether-modified silicone* | 0.5 |
| 5. Trimethyl siloxysilicic acid | 1.0 |
| 6. Octyl p-methoxysilicate | 4.0 |
| 7. Particulate titanium oxide | 8.0 |
| 8. Sorbitol | 2.0 |
| 9. Sodium chloride | 2.0 |
| 10. Preservative | Suitable amount |
| 11. Perfume | Suitable amount |
| 12. Purified water | Remainder |

*KF-6012 (Shin-Etsu Chemical Co., Ltd.)

It was found that the sunscreen milky lotion obtained above had a fine texture, spread easily, was not sticky, had a moist, fresh feel and also lasted well. Its ultraviolet protection effect continued for a long time, it showed no change with regard to temperature or time and it had excellent stability.

Example 31

Essence

An essence was obtained using the following combination.

| (Component) | (%) |
| --- | --- |
| 1. Paste-like silicone composite of Example 4 | 12.0 |
| 2. Triisooctanoic acid glyceride | 10.0 |
| 3. Polyether-modified silicone* | 2.0 |
| 4. Silicone gel** | 0.2 |
| 5. Glycerol | 10.0 |

-continued

| (Component) | (%) |
|---|---|
| 6. Ascorbic acid magnesium phosphate | 3.0 |
| 7. Sodium chloride | 2.0 |
| 8. Preservative | Suitable amount |
| 9. Perfume | Suitable amount |
| 10. Purified water | Remainder |

*KF6017 (Shin-Etsu Chemical Co., Ltd.)
**Silicone gel: KSG21 (Shin-Etsu Chemical Co., Ltd.)

It was found that the essence obtained above had a fine texture, spread easily, was not sticky, and had a moist, fresh feel. It showed no change with regard to temperature or time, and it had excellent stability.

Example 32

Cream

A cream was obtained using the following combination.

| (Component) | (%) |
|---|---|
| 1. Paste-like silicone composite of Example 5 | 18.0 |
| 2. Dimethylpolysiloxane (100 cs) | 2.0 |
| 3. Polypropylene glycol (3) myristyl ether | 0.5 |
| 4. Polyether-modified silicone* | 1.4 |
| 5. Polyether oleyl-modified silicone** | 2.5 |
| 6. Hydrophobically-treated particulate titanium oxide*** | 1.0 |
| 7. Glycerol | 3.0 |
| 8. 70% sorbitol | 5.0 |
| 9. Citric acid | 25.0 |
| 10. Sodium chloride | 0.6 |
| 11. Preservative | Suitable amount |
| 12. Perfume | Suitable amount |
| 13. 32% aqueous ammonia | 4.5 |
| 14. Purified water | Remainder |

*KF-6017 (Shin-Etsu Chemical Co., Ltd.)
**KF-6026 (Shin-Etsu Chemical Co., Ltd.)
***Hydrophobically-treated particulate titanium oxide aluminum stearate-treated particulate titanium oxide It was found that, although the cream obtained above does not contain a large amount of citric acid, it spread easily and was not sticky when applied. After application, it was moist without being sticky, showed no change with regard to temperature or time, and had excellent stability.

Example 33

Aftershave Cream

An aftershave cream was obtained using the following combination.

| (Component) | (%) |
|---|---|
| 1. Paste-like silicone composite of Example 6 | 35.0 |
| 2. Polyether-modified silicone* | 2.9 |
| 3. Polyether oleyl-modified silicone** | 5.0 |
| 4. Polyethylene glycol (molecular weight: 400) | 5.0 |
| 5. L-sodium glutamate | 2.0 |
| 6. Allantoin | 0.1 |
| 7. Aloe extract | Suitable amount |
| 6. Preservative | Suitable amount |
| 9. Antioxidant | Suitable amount |
| 10. Perfume | Suitable amount |
| 11. Purified water | Remainder |

*KF-6017 (Shin-Etsu Chemical Co., Ltd.)
**KF-6026 (Shin-Etsu Chemical Co., Ltd.)

It was found that the aftershave cream obtained above had a high viscosity, and did not drip. It spread easily and was not sticky when applied. After application, it was dry, but very fresh. It was very easy to use, and had excellent stability.

Example 34

Deodorant

A deodorant was obtained using the following combination.

| (Component) | (%) |
|---|---|
| 1. Paste-like silicone composite of Example 3 | 12.0 |
| 2. Dimethyl polysiloxane (6 cs) | 4.0 |
| 3. Polyether-modified silicone* | 1.0 |
| 4. Propylene glycol | 31.0 |
| 5. Triclosan | 0.1 |
| 6. Glycerol | 15.0 |
| 7. Preservative | Suitable amount |
| 8. Perfume | Suitable amount |
| 9. Purified water | Remainder |

*KF-615A (Shin-Etsu Chemical Co., Ltd.)

It was found that the deodorant obtained above did not drip even when used in high concentration, was not sticky, continued to retain its dry effect for a long time and was very easy to use.

Example 35

Liquid Foundation

A liquid foundation was obtained using the following combination.

| (Component) | (%) |
|---|---|
| 1. Paste-like silicone composite of Example 4 | 16.0 |
| 2. Dimethylpolysiloxane (6 cs) | 8.0 |
| 3. Octyl p-methoxy cinnamate | 3.0 |
| 4. 12-hydroxystearic acid | 1.0 |
| 5. Fluorine-modified silicone* | 15.0 |
| 6. Fluorine polyether-modified silicone** | 5.0 |
| 7. Spherical silicone resin powder*** | 3.0 |
| 8. Fluorine compound-treated particulate titanium oxide**** | 8.0 |
| 9. Fluorine compound-treated mica titanium**** | 1.0 |
| 10. Fluorine compound-treated titanium oxide**** | 5.0 |
| 11. Fluorine compound-treated red ocher**** | 0.9 |
| 12. Fluorine compound-treated yellow iron oxide**** | 2.0 |
| 13. Fluorine compound-treated black iron oxide**** | 1.0 |
| 14. Ethanol | 15.0 |
| 15. Glycerol | 3.0 |
| 16. Magnesium sulfate | 1.0 |
| 17. Preservative | Suitable amount |
| 18. Perfume | Suitable amount |
| 19. Purified water | Remainder |

*FPD-6131 (Shin-Etsu Chemical Co., Ltd.)
**FL-100 (Shin-Etsu Chemical Co., Ltd.)
***KMP590 (Shin-Etsu Chemical Co., Ltd.)
****fluorine compound treatment: 5% coverage with diethanolamine salt of perfluoroalkylethylene phosphoric acid.

It was found that the liquid foundation obtained was not sticky, spread easily, and had a clean, very cool feeling. It did not change with temperature or time, and was very stable.

Example 36

Milky Lotion

A milky lotion was obtained using the following combination.

| (Component) | (%) |
| --- | --- |
| 1. Paste-like silicone compound of Example 5 | 15.0 |
| 2. Methylphenyl polysiloxane | 5.0 |
| 3. Squalene | 5.0 |
| 4. Tetra-2-ethylhexanoic acid pentaerythritol | 5.0 |
| 5. Polyether-modified silicone* | 3.0 |
| 6. Organopolysiloxane elastomer spherical powder** | 2.0 |
| 7. Hydrophobic silica*** | 0.5 |
| 8. Ascorbic acid magnesium phosphate | 1.0 |
| 9. Sodium chloride | 1.0 |
| 10. Polyethylene glycol 11000 | 1.0 |
| 11. Propylene glycol | 8.0 |
| 12. Preservative | Suitable amount |
| 13. Perfume | Suitable amount |
| 14. Purified water | Remainder |

*KF-6017 (Shin-Etsu Chemical Co., Ltd.)
**KMP594 (Shin-Etsu Chemical Co., Ltd.)
***Aerogel R972 (made by Japan Aerogel, Inc.)

It was found that the milky lotion obtained spread easily, and was dry without being sticky. It did not change with temperature or time, and was very easy to use and very stable.

Example 37

Moisturing Cream

A moisturing cream was obtained using the following combination.

| (Component) | (%) |
| --- | --- |
| 1. Paste-like silicone composite of Example 6 | 10.0 |
| 2. Methylphenyl polysiloxane | 3.0 |
| 3. Liquid paraffin | 5.0 |
| 4. Pentaerythritol tetra-2-ethyl hexanoate | 3.0 |
| 5. Cetyl 2-ethyl hexanoate | 5.0 |
| 6. Polyether-modified silicone* | 1.0 |
| 7. Organopolysiloxane elastomer spherical powder** | 2.5 |
| 8. Hydrophobic silica*** | 2.0 |
| 9. Zinc stearate | 2.0 |
| 10. Vitamin E acetate | 3.0 |
| 11. Polyethylene glycol 400 | 1.0 |
| 12. Sodium lactate | 1.0 |
| 13. 1,3-butylene glycol | 5.0 |
| 14. Preservative | Suitable amount |
| 15. Perfume | Suitable amount |
| 16. Purified water | Remainder |

*KF-6017 (Shin-Etsu Chemical Co., Ltd.)
**KMP594 (Shin-Etsu Chemical Co., Ltd.)
***Aerogel R972 (made by Japan Aerogel)

It was found that the moisturizing cream obtained spread easily, and was fresh without being sticky. It did not change with temperature or time, and was very easy to use and very stable.

Example 38

Hand Cream

A hand cream was obtained by the following combination.

| (Component) | (%) |
| --- | --- |
| 1. Paste-like silicone composite of Example 3 | 30.0 |
| 2. Liquid paraffin | 10.0 |
| 3. Amino-modified silicone gum* | 15.0 |
| 4. Polyether-modified silicone** | 4.0 |
| 5. Distearyl dimethylammonium chloride | 0.8 |
| 6. Vitamin E acetate | 0.1 |
| 7. Polyethylene glycol 4000 | 1.0 |
| 8. Glycerol | 10.0 |
| 9. Sumectone | 1.2 |
| 10. Preservative | Suitable amount |
| 11. Perfume | Suitable amount |
| 12. Purified water | Remainder |

*70000 g/mol amine equivalent
**KF-6017 (Shin-Etsu Chemical Co., Ltd.)

It was found that the hand cream obtained was not sticky, spread easily and had a clean feel when used. It effectively protects the skin when washing up, etc., and has very high temperature stability.

Example 39

Eyeliner

An eyeliner was obtained using the following combination.

| (Component) | (%) |
| --- | --- |
| 1. Paste-like silicone composite of Example 4 | 22.0 |
| 2. Dimethyl polysiloxane (6 cs) | 5.0 |
| 3. Silicone-treated black iron oxide | 20.0 |
| 4. Vitamin E acetate | 0.2 |
| 5. Jojoba oil | 2.0 |
| 6. Bentonite | 3.0 |
| 7. Polyether-modified silicone* | 2.0 |
| 8. Ethanol | 10.0 |
| 9. 1,3-butylene glycol | 10.0 |
| 10. Preservative | Suitable amount |
| 11. Perfume | Suitable amount |
| 12. Purified water | Remainder |

*KF-6012 (Shin-Etsu Chemical Co., Ltd.)

It was found that the eyeliner obtained spread easily, draws easily and had a cool feel when used, it was clean without being sticky, showed no change with regard to temperature or time, and was very easy and safe to use. It had excellent water resistance and antiperspirant properties, and lasts very well.

Example 40

Cream

A cream was obtained using the following combination.

| (Component) | (%) |
| --- | --- |
| 1. Paste-like silicone composite of Example 5 | 16.0 |
| 2. Dimethyl polysiloxane (6 cs) | 4.0 |
| 3. Polyether-modified silicone* | 5.0 |
| 4. POE(5) octyldodecyl ether | 1.0 |
| 5. Monostearic acid polyoxyethylene sorbitan (20 E.O.) | 0.5 |
| 6. Silicic acid anhydride-treated zinc oxide** | 2.0 |

-continued

| (Component) | (%) |
|---|---|
| 7. Silicone-treated particulate titanium oxide | 10.0 |
| 8. Liquid paraffin | 2.0 |
| 9. Macadamia nut oil | 1.0 |
| 10. Scutellariae radix extract*** | 1.0 |
| 11. Gentian root extract**** | 0.5 |
| 12. Ethanol | 5.0 |
| 13. 1,3-butylene glycol | 2.0 |
| 14. Preservative | Suitable amount |
| 15. Perfume | Suitable amount |
| 16. Purified water | Remainder |

*KF-6012 (Shin-Etsu Chemical Co., Ltd.)
**silicic acid anhydride-treated zinc oxide: - silica of particle diameter 0.01–10 micrometer enclosing 50% zinc oxide; Sansfair SZ-5 (Asahi Glass Co., Ltd.)
***Scutellariae radix extract; extracted with 50% 1,3-butylene glycol water
****Gentian root extract; extracted with 20% ethanol water It was found that the cream obtained above was not sticky, and spread easily. It had excellent adherence, a firm feel and lustrous sheen. It lasted very well, showed no change with temperature or time, and had excellent stability.

Example 41

Foundation

A foundation was obtained using the following combination.

| (Component) | (%) |
|---|---|
| 1. Paste-like silicone composite of Example 6 | 27.0 |
| 2. Methylphenyl polysiloxane | 3.0 |
| 3. Triiso-octanoic acid glyceride | 10.0 |
| 4. Polyether-modified silicone* | 1.0 |
| 5. Polyether oleyl-modified silicone** | 1.0 |
| 6. Monoisostearic acid polyglyceride | 3.0 |
| 7. Hydrophobically-treated mixed powder (Note 1) | 18.0 |
| 8. Red ocher | 1.2 |
| 9. Yellow iron oxide | 2.6 |
| 10. Black iron oxide | 0.2 |
| 11. 1,3-butylene glycol | 7.0 |
| 12. Sodium chloride | 0.5 |
| 13. Preservative | Suitable amount |
| 14. Perfume | Suitable amount |
| 15. Purified water | Remainder |
| (Note 1) Hydrophobically-treated mixed powder | |
| a. Particulate titanium oxide | 8.0 |
| b. Particulate zinc oxide | 4.0 |
| c. Talc | 3.0 |
| d. Mica | 3.0 |

*KF-6017 (Shin-Etsu Chemical Co., Ltd.)
**KF-6026 (Shin-Etsu Chemical Co., Ltd.)

It was found that the foundation obtained above was not sticky, and spread easily. It had excellent adherence, a firm feel and lustrous sheen. It lasted very well, showed no change with temperature or time, and had excellent stability.

Example 42

Sun-cut Cream

A sun-cut cream was obtained using the following combination.

| (Component) | (%) |
|---|---|
| 1. Paste-like silicone composite of Example 3 | 17.5 |
| 2. KP545* | 12.0 |
| 3. Triiso-octanoic acid glyceride | 5.0 |
| 4. Octyl p-methoxysilicic acid | 6.0 |
| 5. KSG21** | 5.0 |
| 6. Polyether-modified silicone*** | 1.0 |
| 7. Lipophilic-treated zinc oxide | 20.0 |
| 8. Sodium chloride | 0.5 |
| 9. 1,3-butylene glycol | 2.0 |
| 10. Preservative | Suitable amount |
| 11. Perfume | Suitable amount |
| 12. Purified water | Remainder |

*KP545: acrylic silicone resin/50%-D5 solution (Shin-Etsu Chemical Co., Ltd.)
**KSG21: silicone gel (Shin-Etsu Chemical Co., Ltd.)
***KF-6017 (Shin-Etsu Chemical Co., Ltd.)

It was found that the sun-cut cream obtained above was not sticky, and spread easily. It had excellent adherence, a firm feel and lustrous sheen. It lasted very well, showed no change with temperature or time, and had excellent stability.

Example 43

O/W Hand Cream

A hand cream was obtained using the following combination.

| (Component) | (%) |
|---|---|
| 1. Acrylic silicone resin/M3T, 50% solution | 10.0 |
| 2. Paste-like silicone composite of Example 4 | 2.0 |
| 3. Isoparaffin | 5.0 |
| 4. Vaseline | 5.0 |
| 5. Triiso-octanoic acid glyceride | 3.0 |
| 6. Polyether-modified silicone** | 0.5 |
| 7. Mono-oleic acid polyoxyethylene sorbitan | 1.0 |
| 8. Sepigel 305*** | 2.0 |
| 9. 1,3-butylene glycol | 5.0 |
| 10. Glycerol | 5.0 |
| 11. Preservative | Suitable amount |
| 12. Perfume | Suitable amount |
| 13. Purified water | Remainder |

**KF-6017 (Shin-Etsu Chemical Co., Ltd.)
***Sepigel 305: (made by SEPPIC)

It was found that the hand cream obtained above was not sticky, and spread easily. It had excellent adherence, a firm feel and lustrous sheen. It lasted very well, showed no change with temperature or time, and had excellent stability.

Example 44

O/W Hand Cream

A hand cream was obtained using the following combination.

| (Component) | (%) |
|---|---|
| 1. Acrylic silicone resin/M3T, 50% solution | 10.0 |
| 2. Stearyl-modified acryl silicone | 8.0 |
| 3. Cetanol | 1.0 |
| 4. Triisostearic acid glyceride | 5.0 |

-continued

| (Component) | (%) |
|---|---|
| 5. Stearic acid | 3.0 |
| 6. Monostearic acid glyceride | 1.5 |
| 7. Paste-like silicone composite of Example 5 | 0.7 |
| 8. Sesquioleic acid sorbitan | 0.5 |
| 9. Mono-oleic acid polyoxyethylene sorbitan | 1.0 |
| 10. Sodium hydroxide (1% aqueous solution) | 10.0 |
| 11. 1,3-butylene glycol | 5.0 |
| 12. Preservative | Suitable amount |
| 13. Perfume | Suitable amount |
| 14. Purified water | Remainder |

It was found that the hand cream obtained above was not sticky, and spread easily. It had excellent adherence, a firm feel and lustrous sheen. It lasted very well, showed no change with temperature or time, and had excellent stability.

Example 45

Aerosol Composite

The aerosol composite was obtained by the following combination.

| (Component) | (%) |
|---|---|
| 1. Silicone-treated mica | 3.0 |
| 2. Aluminum chlorhydroxy | 2.0 |
| 3. Isopropyl methyl phenol | 0.3 |
| 4. Sesquioleic acid sorbitan | 0.2 |
| 5. Isopropyl myristate | 5.0 |
| 6. Paste-like silicone composite of Example 6 | 5.0 |
| 7. Perfume | Suitable amount |
| 8. Injection agent | Remainder |

It was found that the aerosol composite of this invention obtained above had a strong deodorant effect, was not sticky or heavy to use, spread easily, and had a dry, smooth feel. As it had good re-dispersibility, it was very easy to use.

Example 46

Antiperspirant

A refined antiperspirant was obtained using the following combination.

| (Component) | (%) |
|---|---|
| 1. Paste-like silicone composite of Example 4 | 20.0 |
| 2. KSG-15 | 20.0 |
| 3. M3T | 30.0 |
| 4. Aluminum zirconium tetrachlorohydrex GLY | 20.0 |
| 5. KF-96(6 CS) | 10.0 |

It was found that the antiperspirant obtained above was not sticky, spread easily, and was very stable with regarding to temperature and time.

Example 47

Eye Wrinkle Cream

An eye wrinkle cream was obtained using the following combination.

| (Component) | (%) |
|---|---|
| 1. Paste-like silicone composite of Example 4 | 20.0 |
| 2. Trimethylsiloxy silicate | 5.0 |
| 3. Polyether-modified siloxane* | 2.0 |
| 4. Polyether oleyl-modified silicone** | 5.0 |
| 5. Sodium chondroitin sulfate | 2.0 |
| 6. Sodium lactate | 1.0 |
| 7. Glycerol | 50.0 |
| 8. Preservative | Suitable amount |
| 9. Antioxidant | Suitable amount |
| 10. Perfume | Suitable amount |
| 11. Purified water | Remainder |

*KF-6017 (Shin-Etsu Chemical Co., Ltd.)
**KF-6026 (Shin-Etsu Chemical Co., Ltd.)

It was found that the eye wrinkle cream obtained above spread easily, was not sticky or oily, and had a moist, fresh, clean feel when used. It lasted well, showed no change with temperature or time, and was very stable.

From the above, it is clear that by blending the paste-like silicon composite of this invention, a cosmetic material is obtained having improved lasting properties, spreading properties and a smooth feel, and which permits cosmetic products to be easily manufactured. In addition, it is possible to provide a cosmetic material which shows no change with temperature or time; and has excellent stability.

What is claimed is:

1. A silicone polymer having a three-dimensional crosslinked structure obtained by polymerizing:

at least one of:

an organohydrogen polysiloxane of the formula (A1):

$$R^1_a R^2_b H_c SiO_{(4-a-b-c)/2} \tag{A1}$$

and, an organohydrogen polysiloxane of the formula (A2):

$$R^1_d H_e SiO_{(4-d-e)/2} \tag{A2},$$

and;

at least one of:

a polyoxyalkylene of the formula (B1):

$$C_f H_{2f-1}(C_g H_{2g}O)_h C_f H_{2f-1} \tag{B1}$$

a polyoxyalkylene of the formula (B2):

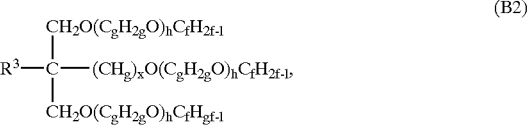

(B2)

a polyoxyalkylene of the formula (B3):

(B3)

and, an organopolyoxy alkylene (B4) of the formula (B4):

which silicone polymer is capable of containing or dissolving and swelling its same weight or more of pentane-3,3,3-trifluoropropyl pentamethylcyclopentasiloxane wherein, in the formulae:

$R^1$, which may be the same or different, is a hydrocarbon group having 1 to 20 carbon atoms, which does not contain an aliphatic unsaturated bond and which is optionally substituted or unsubstituted, provided that 11 to 60 mole % of the $R^1$ groups are a fluorine-substituted monovalent hydrocarbon group, $R^2$, which may be the same or different, is an organic group of the formula —$C_fH_{2f}O(C_gH_{2g}O)_hR^6$, $R^3$, which may be the same or different, is a hydrogen atom or a monofunctional hydrocarbon group containing 1 to 10 carbon atoms which does not contain aliphatic unsaturated bonds and which is optionally substituted or unsubstituted, $R^4$, which may be the same or different, is an organic group identical to $R^3$ or is —$C_fH_{2f-1}$, $R^5$ is a monofunctional hydrocarbon group having 2 to 10 carbon atoms containing a terminal vinyl group, and $R^6$ is a hydrogen atom or a monofunctional hydrocarbon group or acetyl group not containing aliphatic unsaturated groups, which is optionally substituted or unsubstituted, a is about 1.0–2.3, b is about 0.001 to 1.0, c is about 0.001–1.0, d is about 1.0–2.3, e is about 0.001–1.0, j is about 1.0–2.3, and k is about 0.001–1.0, and about $1.5 \leq a+b+c \leq$ about 2.6, about $1.5 \leq d+e \leq$ about 2.6, about $1.5 \leq j+k \leq$ about 2.6, f is an integer in the range 2–6, g is 2, 3 or 4, h is an integer in the range 1–200, i is an integer in the range 2–20, and x is 0 or 1.

2. The silicone polymer as defined in claim 1, produced by polymerizing the organohydrogen polysiloxane of formula (A2) and the polyoxyalkylene of formula (B1).

3. The silicone polymer as defined in claim 1, produced by polymerizing the organohydrogen polysiloxane of formula (A2) and the organopolysiloxane of formula (B4).

4. A paste-like silicone composition obtained by kneading a mixture of 100 weight parts of said silicone polymer of claim 1 and 10–1000 weight parts of a fluorine-modified silicone oil, which is of the formula (C):

having a viscosity of less than about 200 mm²/s at 25 degree C., $R^1$, which may be identical or different, are monofunctional hydrocarbon groups having 1 to 20 carbon atoms not containing an aliphatic unsaturated bond which are optionally substituted or unsubstituted, provided that about 11–60 mole % of the $R^1$ groups are a fluorine-substituted monofunctional hydrocarbon group, and m is 1.8–2.3.

5. The paste-like silicone composition as defined in claim 4, wherein said fluorine-modified silicone oil has the following average empirical formula:

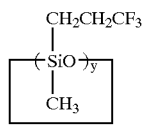

wherein, y is an integer from 4–6.

6. A cosmetic material formed by blending the paste-like silicone composition as defined in claim 4.

7. A cosmetic material, comprising a) the paste-like silicone composition as defined in claim 4, b) an oil and c) a compound having an alcoholic hydroxyl group in the molecular structure, wherein the blending amount of the a) paste-like silicone composition in the cosmetic material is 0.1–70.0 wt %.

8. The cosmetic material as defined in claim 7, wherein at least part of said b) oil is a liquid at ordinary temperature.

9. The cosmetic material as defined in claim 7, wherein at least part of said oil b) is selected from the group consisting of a silicone oil comprising a volatile silicone, and an oil having a repeating unit of —[O—Si—]n in the molecular skeleton.

10. The cosmetic material as defined in claim 7, wherein said compound c) having an alcoholic hydroxyl group in the molecular structure is a water-soluble, and monofunctional or polyfunctional alcohol.

11. The cosmetic material as defined in claim 7, wherein at least part of said oil b) comprises a fluorine group or an amino group.

12. The cosmetic material as defined in claim 7, wherein the blending amount of said oil b) is approximately 0.1 to 50.0 wt %.

13. The cosmetic material as defined in claim 7, wherein the blending amount of said compound c) having an alcoholic hydroxyl group in the molecular structure is approximately 0.1 to 70.0 wt %.

14. The cosmetic material as defined in claim 7, wherein said compound c) having an alcoholic hydroxyl group in the molecular structure is a water-soluble polymer.

15. The cosmetic material as defined in claim 7, further comprising at least one of: d) water, e) a powder and/or colorant, f) a surfactant, g) a crosslinked organopolysiloxane not containing a fluorine-substituted alkyl group, h) a silicone resin, and i) an ultraviolet protecting component.

16. The cosmetic material as defined in claim 15, wherein the material comprises a powder and/or colorant, e), at least part of which is at least one of a powder having a silicon resin and silicone elastomer as skeleton, and an organic powder having —[O—Si—]n— as structural repeating unit in the molecular skeleton.

17. The cosmetic material as defined in claim 15, wherein the material comprises a surfactant, f), which is a modified silicone having a polyoxy alkylene chain in the molecule.

18. The cosmetic material as defined in claim 17, wherein said modified silicone is of the following formula (D):

wherein, in the formula, $R^2$ are identical or different, and are organic groups of the formula —$C_fH_{2f}O(C_gH_{2g}O)_hR^6$, $R^3$ is a hydrogen atom or a monofunctional hydrocarbon group having 1 to 10 carbon atoms not containing aliphatic unsaturated bonds, and which is optionally substituted or unsubstituted, $R^6$ is a hydrogen atom or a monofunctional hydrocarbon group or acetone group not containing aliphatic unsaturated groups and which is optionally substituted or unsubstituted, R⁷ is a fluorine-substituted monofunctional hydrocarbon group not containing aliphatic unsaturated bonds, p is about 1.0–2.0, q is about 0.001–1.0, r is about 0.001–1.0, and about $1.55 \leq p+q+r \leq$ about 2.6).

19. The cosmetic material as defined in claim 15, wherein the material comprises a surfactant with an HLB of 1–18.

20. The cosmetic material as defined in claim 15, wherein said material comprises a crosslinked organopolysiloxane not containing fluorine-substituted alkyl groups, g), which is capable of containing or dissolving at least its own weight of a silicone having a viscosity of 0.65–100 mm²/s, and swells up.

21. The cosmetic material as defined in claim 15, wherein said material comprises a crosslinked organopolysiloxane not containing fluorine-substituted alkyl groups, g), which is a crosslinked organopolysiloxane which forms a crosslinked structure by reacting an organopolysiloxane having at least an average of 1.5 vinylic reactive sites, and an organopolysiloxane having at least an average of 1.5 hydrogen atoms directly bonded to silicon atoms, in the molecule.

22. The cosmetic material as defined in claim 15, wherein said material comprises a crosslinked organopolysiloxane not containing fluorine-substituted alkyl groups, which is a crosslinked organopolysiloxane comprising at least one of a polyoxyalkyl part, alkyl part, alkenyl part and aryl part in the crosslinked molecule.

23. The cosmetic material as defined in claim 15, wherein said material comprises a silicone resin, h), which is an acrylic silicone.

24. The cosmetic material as defined in claim 23, wherein said acrylic silicone contains at least one of a pyrrolidone part, long chain alkyl part, polyoxy alkylene part and fluoroalkyl part in the molecule.

25. The cosmetic material as defined in claim 15, wherein said material comprises a silicone resin, h), which is a silicone lattice compound.

26. The cosmetic material as defined in claim 25, wherein said silicone lattice compound contains at least one of a pyrrolidone part, long chain alkyl part, polyoxyalkylene part, fluoroalkyl part and amino part.

27. The cosmetic material as defined in claim 6, wherein the form of product is a liquid, emulsion, cream, solid, paste, gel, powder, laminate, mousse or spray.

28. The cosmetic material as defined in claim 6, wherein at least part of the components of the cosmetic material is a skincare cosmetic material.

29. The cosmetic material as defined in claim 6, wherein at least part of the components of the cosmetic material is a hair treatment cosmetic material.

30. The cosmetic material as defined in claim 6, wherein at least part of the components of the cosmetic material is an antiperspirant cosmetic material.

31. The cosmetic material as defined in claim 6, wherein at least part of the components of the cosmetic material is a makeup cosmetic material.

32. The cosmetic material as defined in claim 6, wherein at least part of the components of the cosmetic material is an ultraviolet protection cosmetic material.

33. The skincare cosmetic material as defined in claim 28, wherein the form of product is a liquid, emulsion, cream, solid, paste, gel, powder, laminate, mousse or spray.

34. The hair treatment cosmetic material as defined in claim 29, wherein the form of product is a liquid, emulsion, cream, solid, paste, gel, powder, laminate, mousse or spray.

35. The antiperspirant cosmetic material as defined in claim 30, wherein the form of product is a liquid, emulsion, cream, solid, paste, gel, powder, laminate, mousse or spray.

36. The makeup cosmetic material as defined in claim 31, wherein the form of product is a liquid, emulsion, cream, solid, paste, gel, powder, laminate, mousse or spray.

37. The ultraviolet protection cosmetic material as defined in claim 32, wherein the form of product is a liquid, emulsion, cream, solid, paste, gel, powder, laminate, mousse or spray.

* * * * *